(12) United States Patent
Biron-Sorek et al.

(10) Patent No.: US 10,871,487 B2
(45) Date of Patent: Dec. 22, 2020

(54) FRET-BASED GLUCOSE-DETECTION MOLECULES

(71) Applicant: GLUSENSE LTD., Rehovot (IL)

(72) Inventors: Zohar Biron-Sorek, Rehovot (IL); Uriel Barkai, MP Hof-Carmel (IL)

(73) Assignee: GLUSENSE LTD., Rehovot (IL)

( * ) Notice: Subject to any disclaimer, the term of this patent is extended or adjusted under 35 U.S.C. 154(b) by 0 days.

(21) Appl. No.: 16/094,759

(22) PCT Filed: Apr. 19, 2017

(86) PCT No.: PCT/IL2017/050456
§ 371 (c)(1),
(2) Date: Oct. 18, 2018

(87) PCT Pub. No.: WO2017/183030
PCT Pub. Date: Oct. 26, 2017

(65) Prior Publication Data
US 2019/0128879 A1 May 2, 2019

Related U.S. Application Data

(60) Provisional application No. 62/325,136, filed on Apr. 20, 2016.

(51) Int. Cl.
*G01N 33/542* (2006.01)
*G01N 33/66* (2006.01)
*C12Q 1/54* (2006.01)

(52) U.S. Cl.
CPC ............. *G01N 33/542* (2013.01); *C12Q 1/54* (2013.01); *G01N 33/66* (2013.01)

(58) Field of Classification Search
None
See application file for complete search history.

(56) References Cited

U.S. PATENT DOCUMENTS

| | | |
|---|---|---|
| 3,486,506 A | 12/1969 | Auphan |
| 3,554,199 A | 1/1971 | Auphan |
| 3,774,243 A | 11/1973 | Ng et al. |
| 3,826,265 A | 7/1974 | Giori et al. |
| 3,837,339 A | 9/1974 | Aisenberg et al. |
| 3,837,922 A | 9/1974 | Ng et al. |
| 3,861,397 A | 1/1975 | Rao et al. |
| 4,140,963 A | 2/1979 | Rao et al. |
| 4,344,438 A | 8/1982 | Schultz |
| 4,352,883 A | 10/1982 | Lim |
| 4,402,694 A | 9/1983 | Ash et al. |
| 4,453,537 A | 6/1984 | Spitzer |
| 4,578,323 A | 3/1986 | Hertl et al. |
| 4,631,053 A | 12/1986 | Taheri |
| 4,661,107 A | 4/1987 | Fink |
| 4,721,677 A | 1/1988 | Clark, Jr. |
| 4,745,279 A | 5/1988 | Karkar et al. |
| 4,801,291 A | 1/1989 | Loori |
| 4,953,976 A | 9/1990 | Adler-Golden et al. |
| 4,981,779 A | 1/1991 | Wagner |
| 5,001,054 A | 3/1991 | Wagner |
| 5,011,472 A | 4/1991 | Aebischer et al. |
| 5,029,579 A | 7/1991 | Trammell |
| 5,089,697 A | 2/1992 | Prohaska |
| 5,101,814 A | 4/1992 | Palti |
| 5,116,494 A | 5/1992 | Chick et al. |
| 5,143,066 A | 9/1992 | Komives et al. |
| 5,209,231 A | 5/1993 | Cote et al. |
| 5,246,867 A | 9/1993 | Lakowicz et al. |
| 5,262,055 A | 11/1993 | Bae |
| 5,336,209 A | 8/1994 | Porzilli |
| 5,368,028 A | 11/1994 | Palti |
| 5,372,135 A | 12/1994 | Mendelson et al. |
| 5,373,855 A | 12/1994 | Skrabal et al. |
| 5,381,075 A | 1/1995 | Jordan |
| 5,387,522 A | 2/1995 | Vasington |
| 5,407,685 A | 4/1995 | Malchesky |
| 5,427,935 A | 6/1995 | Wang et al. |
| 5,431,694 A | 7/1995 | Snaper et al. |
| 5,443,504 A | 8/1995 | Hill |
| 5,443,508 A | 8/1995 | Giampapa |
| 5,512,474 A | 4/1996 | Clapper et al. |
| 5,529,066 A | 6/1996 | Palti |
| 5,545,191 A | 8/1996 | Mann et al. |
| 5,578,022 A | 11/1996 | Scherson |
| 5,614,378 A | 3/1997 | Yang et al. |
| 5,626,134 A | 5/1997 | Zuckerman |
| 5,660,940 A | 8/1997 | Larsson et al. |
| 5,662,625 A | 9/1997 | Geary, Jr. |
| 5,702,444 A | 12/1997 | Struthers et al. |
| 5,713,888 A | 2/1998 | Neuenfeldt |

(Continued)

FOREIGN PATENT DOCUMENTS

| | | |
|---|---|---|
| AU | 2011253785 | 1/2012 |
| CN | 101278829 | 10/2008 |

(Continued)

OTHER PUBLICATIONS

An International Preliminary Report on Patentability dated Jun. 29, 2011 which issued during the prosecution of Applicant's PCT/IL 09/01214.

An International Search Report and a Written Opinion both dated Apr. 30, 2010 which issued during the prosecution of Applicant's PCT/IL 09/01214.

U.S. Appl. No. 61/746,691, filed Dec. 28, 2012.

An International Preliminary Report on Patentability dated Mar. 24, 2009 which issued during the prosecution of Applicant's PCT/IL2005/000743.

Written Opinion dated Mar. 20, 2009 which issued during the prosecution of Applicant's PCT/IL2005/000743.

An International Search Report dated May 7, 2009 which issued during the prosecution of Applicant's PCT/IL2005/000743.

(Continued)

*Primary Examiner* — Iqbal H Chowdhury
(74) *Attorney, Agent, or Firm* — Sughrue Mion, PLLC

(57) ABSTRACT

Proteins (20) having glucose-binding sites (28) that bind to glucose (30) are described.

22 Claims, 4 Drawing Sheets
Specification includes a Sequence Listing.

(56) References Cited

U.S. PATENT DOCUMENTS

| | | |
|---|---|---|
| 5,741,334 A | 4/1998 | Mullon et al. |
| 5,770,454 A | 6/1998 | Essenpreis et al. |
| 5,788,682 A | 8/1998 | Maget |
| 5,792,090 A | 8/1998 | Ladin |
| 5,833,603 A | 11/1998 | Kovacs et al. |
| 5,834,005 A | 11/1998 | Usala |
| 5,855,570 A | 1/1999 | Scherson |
| 5,855,613 A | 1/1999 | Antanavich et al. |
| 5,879,709 A | 3/1999 | Soon-Shiong et al. |
| 5,902,745 A | 5/1999 | Butler et al. |
| 5,912,005 A | 6/1999 | Lanza et al. |
| 5,998,204 A | 12/1999 | Tsien et al. |
| 6,000,403 A | 12/1999 | Cantwell |
| 6,049,727 A | 4/2000 | Crothall |
| 6,049,728 A | 4/2000 | Chou |
| 6,061,582 A | 5/2000 | Small et al. |
| 6,091,974 A | 7/2000 | Palti |
| 6,148,232 A | 11/2000 | Avrahami |
| 6,163,714 A | 12/2000 | Stanley et al. |
| 6,179,804 B1 | 1/2001 | Satterfield |
| 6,187,043 B1 | 2/2001 | Ledergerber |
| 6,188,477 B1 | 2/2001 | Pu et al. |
| 6,197,534 B1 | 3/2001 | Lakowicz et al. |
| 6,254,601 B1 | 7/2001 | Burbank et al. |
| 6,256,522 B1 | 7/2001 | Schultz |
| 6,268,161 B1 | 7/2001 | Han |
| 6,294,281 B1 | 9/2001 | Heller |
| 6,330,464 B1 | 12/2001 | Colvin, Jr. et al. |
| 6,349,234 B2 | 2/2002 | Pauly et al. |
| 6,368,592 B1 | 4/2002 | Colton et al. |
| 6,372,244 B1 | 4/2002 | Antanavich |
| 6,383,478 B1 | 5/2002 | Prokop |
| 6,400,974 B1 | 6/2002 | Lesho |
| 6,471,687 B2 | 10/2002 | Butler et al. |
| 6,485,703 B1 | 11/2002 | Cote et al. |
| 6,521,446 B2 | 2/2003 | Hellinga |
| 6,531,239 B2 | 3/2003 | Heller |
| 6,556,867 B1 | 4/2003 | Kohls |
| 6,577,393 B1 | 6/2003 | Potzschke et al. |
| 6,584,335 B1 | 6/2003 | Haar et al. |
| 6,587,704 B1 | 7/2003 | Fine et al. |
| 6,602,251 B2 | 8/2003 | Burbank et al. |
| 6,605,039 B2 | 8/2003 | Houben et al. |
| 6,625,479 B1 | 9/2003 | Weber et al. |
| 6,630,154 B1 | 10/2003 | Fraker et al. |
| 6,650,919 B2 | 11/2003 | Edelberg et al. |
| 6,666,821 B2 | 12/2003 | Keimel |
| 6,671,527 B2 | 12/2003 | Petersson et al. |
| 6,673,596 B1 | 1/2004 | Sayler et al. |
| RE38,525 E | 6/2004 | Stanley et al. |
| 6,764,488 B1 | 7/2004 | Burbank et al. |
| 6,766,183 B2 | 7/2004 | Walsh et al. |
| 6,767,342 B1 | 7/2004 | Cantwell |
| 6,804,544 B2 | 10/2004 | Van Antwerp et al. |
| 6,821,107 B1 | 11/2004 | Hara |
| 6,846,288 B2 | 1/2005 | Nagar et al. |
| 6,855,556 B2 | 2/2005 | Amiss et al. |
| 6,960,351 B2 | 11/2005 | Dionne |
| 6,979,088 B2 | 12/2005 | Currie |
| 6,979,290 B2 | 12/2005 | Mourlas et al. |
| 7,068,867 B2 | 6/2006 | Adoram et al. |
| 7,161,679 B2 | 1/2007 | Masseschmidt et al. |
| 7,184,810 B2 | 2/2007 | Caduff et al. |
| 7,208,286 B2 | 4/2007 | Simpson et al. |
| 7,223,279 B2 | 5/2007 | Burbank et al. |
| 7,259,906 B1 | 8/2007 | Islam |
| 7,325,546 B2 | 2/2008 | Burbank et al. |
| 7,489,402 B2 | 2/2009 | Selker et al. |
| 7,729,767 B2 | 6/2010 | Baker et al. |
| 7,771,357 B2 | 8/2010 | Burbank et al. |
| 7,775,975 B2 | 8/2010 | Brister et al. |
| 7,863,038 B2 | 1/2011 | Motamedi et al. |
| 7,892,222 B2 | 2/2011 | Vardi et al. |
| 7,951,357 B2 | 5/2011 | Gross et al. |
| 7,964,390 B2 | 6/2011 | Rozakis et al. |
| 8,012,500 B2 | 9/2011 | Rotem |
| 8,043,271 B2 | 10/2011 | Stern |
| 8,088,595 B2 | 1/2012 | Ibey et al. |
| 8,204,565 B2 | 6/2012 | Arnold et al. |
| 8,444,630 B2 | 5/2013 | Rotem |
| 8,700,115 B2 | 4/2014 | Markle et al. |
| 8,738,107 B2 | 5/2014 | Markle et al. |
| 9,037,205 B2 | 5/2015 | Gil et al. |
| 2002/0016535 A1 | 2/2002 | Martin et al. |
| 2002/0025469 A1 | 2/2002 | Heller |
| 2002/0038083 A1 | 3/2002 | Houben et al. |
| 2002/0072657 A1 | 6/2002 | Bousquet et al. |
| 2002/0120186 A1 | 8/2002 | Keimel |
| 2002/0193672 A1 | 12/2002 | Walsh et al. |
| 2003/0050622 A1 | 3/2003 | Humes |
| 2003/0087427 A1 | 5/2003 | Colton et al. |
| 2003/0113302 A1 | 6/2003 | Revazova |
| 2003/0117629 A1 | 6/2003 | Messerschmidt et al. |
| 2003/0134346 A1 | 7/2003 | Amiss et al. |
| 2003/0216759 A1 | 11/2003 | Burbank et al. |
| 2003/0227681 A1 | 12/2003 | Currie |
| 2003/0232370 A1 | 12/2003 | Trifiro |
| 2004/0091757 A1 | 5/2004 | Wang et al. |
| 2004/0097788 A1 | 5/2004 | Mourlas et al. |
| 2004/0109302 A1 | 6/2004 | Yoneda et al. |
| 2004/0111018 A1 | 6/2004 | Isenberg et al. |
| 2004/0133188 A1 | 7/2004 | Vardi et al. |
| 2004/0199059 A1 | 10/2004 | Brauker et al. |
| 2004/0259270 A1 | 12/2004 | Wolf |
| 2005/0025680 A1 | 2/2005 | Monzyk |
| 2005/0027332 A1 | 2/2005 | Avrahami et al. |
| 2005/0054100 A1 | 3/2005 | Rennard et al. |
| 2005/0085868 A1 | 4/2005 | Tehrani et al. |
| 2005/0095174 A1 | 5/2005 | Wolf |
| 2005/0096516 A1 | 5/2005 | Soykan et al. |
| 2005/0113852 A1 | 5/2005 | Burbank et al. |
| 2005/0118726 A1 | 6/2005 | Schultz et al. |
| 2005/0136092 A1 | 6/2005 | Rotem |
| 2005/0211572 A1 | 9/2005 | Buck et al. |
| 2005/0221072 A1 | 10/2005 | Dubrow et al. |
| 2005/0221276 A1 | 10/2005 | Rozakis et al. |
| 2005/0267326 A1 | 12/2005 | Loeb et al. |
| 2006/0000479 A9 | 1/2006 | Burbank et al. |
| 2006/0063140 A1 | 3/2006 | Nussinovitch |
| 2006/0184206 A1 | 8/2006 | Baker et al. |
| 2006/0241365 A1 | 10/2006 | Botvinick et al. |
| 2007/0003994 A1 | 1/2007 | Simpsonss |
| 2007/0004974 A1 | 1/2007 | Nagar et al. |
| 2007/0066877 A1 | 3/2007 | Arnold et al. |
| 2007/0190038 A1 | 8/2007 | Suzuki |
| 2008/0086042 A1 | 4/2008 | Brister |
| 2008/0166329 A1 | 7/2008 | Sung et al. |
| 2008/0188722 A1 | 8/2008 | Markle et al. |
| 2008/0262567 A1 | 10/2008 | Avrahami et al. |
| 2008/0287776 A1 | 11/2008 | Ephrath et al. |
| 2008/0319287 A1 | 12/2008 | Gross et al. |
| 2009/0012502 A1 | 1/2009 | Rotem |
| 2009/0178459 A1 | 7/2009 | Li et al. |
| 2009/0192493 A1 | 7/2009 | Meng et al. |
| 2009/0287060 A1 | 11/2009 | Pell et al. |
| 2010/0015709 A1 | 1/2010 | Rehfeldt et al. |
| 2010/0037329 A1* | 2/2010 | Frommer ............ C12Q 1/6818 800/13 |
| 2010/0047311 A1 | 2/2010 | Rotem |
| 2010/0145317 A1 | 6/2010 | Laster et al. |
| 2010/0160749 A1 | 6/2010 | Gross et al. |
| 2010/0202966 A1 | 8/2010 | Gross et al. |
| 2010/0312165 A1 | 12/2010 | Stern |
| 2011/0165219 A1 | 7/2011 | Barkai et al. |
| 2011/0190679 A1 | 8/2011 | Humes et al. |
| 2011/0251471 A1 | 10/2011 | Gross et al. |
| 2012/0059232 A1 | 3/2012 | Gross et al. |
| 2012/0113997 A1 | 5/2012 | Islam |
| 2012/0290043 A1 | 11/2012 | Gross |
| 2013/0006069 A1 | 1/2013 | Gil et al. |
| 2013/0116664 A1 | 5/2013 | Tai et al. |
| 2013/0331667 A1 | 12/2013 | Colvin, Jr. et al. |
| 2014/0018644 A1 | 1/2014 | Colvin, Jr. et al. |
| 2014/0088383 A1 | 3/2014 | Colvin, Jr. et al. |

(56) References Cited

U.S. PATENT DOCUMENTS

| | | | |
|---|---|---|---|
| 2014/0187878 | A1 | 7/2014 | Emken et al. |
| 2015/0343093 | A1 | 12/2015 | Gladnikoff et al. |
| 2015/0352229 | A1 | 12/2015 | Brill et al. |
| 2016/0324449 | A1 | 11/2016 | Brill et al. |
| 2017/0072074 | A1 | 3/2017 | Gladnikoff et al. |
| 2017/0100598 | A1 | 4/2017 | Brill et al. |
| 2017/0303838 | A1 | 10/2017 | Brill |

FOREIGN PATENT DOCUMENTS

| | | |
|---|---|---|
| EP | 01351623 | 6/2005 |
| EP | 1645243 | 12/2007 |
| EP | 2196795 | 6/2010 |
| EP | 2004241 | 8/2013 |
| EP | 1786834 | 2/2016 |
| GB | 2024012 | 1/1980 |
| WO | 90/15526 | 12/1990 |
| WO | 91/01680 | 2/1991 |
| WO | 91/09312 | 6/1991 |
| WO | 1992/019195 | 11/1992 |
| WO | 1994/000602 | 1/1994 |
| WO | 1994/020076 | 9/1994 |
| WO | 96/00106 | 1/1996 |
| WO | 98/54294 | 12/1998 |
| WO | 98/55869 | 12/1998 |
| WO | 2000/078920 | 12/2000 |
| WO | 01/50983 | 7/2001 |
| WO | 03/011445 | 2/2003 |
| WO | 03/025220 | 3/2003 |
| WO | 04/028358 | 4/2004 |
| WO | 04/051774 | 6/2004 |
| WO | 04/089465 | 10/2004 |
| WO | 2005/002467 | 1/2005 |
| WO | 2005/033659 | 4/2005 |
| WO | 05/053523 | 6/2005 |
| WO | 06/006166 | 1/2006 |
| WO | 2006/044612 | 4/2006 |
| WO | 2006/059322 | 6/2006 |
| WO | 06/097933 | 9/2006 |
| WO | 07/110867 | 10/2007 |
| WO | 08/018079 | 2/2008 |
| WO | 2008/062417 | 5/2008 |
| WO | 2008/065660 | 6/2008 |
| WO | 2008/079997 | 7/2008 |
| WO | 2009/031154 | 3/2009 |
| WO | 2009/039207 | 3/2009 |
| WO | 2009/140757 | 11/2009 |
| WO | 2010/032242 | 3/2010 |
| WO | 2010/061387 | 6/2010 |
| WO | 2010/073249 | 7/2010 |
| WO | 2010/089739 | 8/2010 |
| WO | 2011/072401 | 6/2011 |
| WO | 2013/001532 | 1/2013 |
| WO | 2013/155553 | 10/2013 |
| WO | 2014/102743 | 7/2014 |
| WO | 2015/079436 | 6/2015 |
| WO | 2015/128826 | 9/2015 |
| WO | 2016/059635 | 4/2016 |
| WO | 2017/183030 | 10/2017 |

OTHER PUBLICATIONS

European Search Report dated Dec. 16, 2009, which issued during the prosecution of Applicant's European Patent Application No. EP 05 75 8905.
A Supplementary European Search Report dated Mar. 3, 2010 which issued during the prosecution of Applicant's European Patent Application No. 05758905.3.
An International Search Report dated Nov. 23, 2007 which issued during the prosecution of Applicant's PCT/IL2007/000399.
An International Preliminary Report on Patentability together with Written Opinion dated Sep. 30, 2008 which issued during the prosecution of Applicant's PCT/IL2007/000399.
An Office Action dated Jan. 13, 2012, which issued during the prosecution of European Patent Application No. 05758905.3.
An Office Action dated Sep. 23, 2011 which issued during the prosecution of U.S. Appl. No. 12/225,749.
A Supplementary European Search Report dated Feb. 4, 2010 which issued during the prosecution of Applicant's European Patent Application No. 07736139.2.
An Office Action dated Oct. 3, 2012, which issued during the prosecution of U.S. Appl. No. 12/344,103.
An Office Action dated Nov. 16, 2011 which issued during the prosecution of European Patent Application No. 07736139.2.
U.S. Appl. No. 60/820,130, filed Jul. 24, 2006.
U.S. Appl. No. 60/658,716, filed Mar. 3, 2005.
U.S. Appl. No. 60/588,211, filed Jul. 14, 2004.
Wan Q, "Dual wavelength polarimetry for monitoring glucose in the presence of varying birefringence," A thesis submitted to the Office of Graduate Studies of Texas A&M University (2004).
Klueh U. et al., entitled, "Enhancement of implantable glucose sensor function in vivo using gene transfer-induced neovascularization," Biomaterials, Apr. 2005.
An Office Action dated Feb. 2, 2012, which issued during the prosecution of U.S. Appl. No. 12/225,749.
Yu-Lung L et al., "A polarimetric glucose sensor using a liquid-crystal polarization modulator driven by a sinusoidal signal," Optics Communications 259(1), pp. 40-48 (2006).
Olesberg JT et al., "Tunable Laser Diode System for Noninvasive Blood Glucose Measurements," Appl. Spectrosc. 59, pp. 1480-1484 (2005).
Olesberg JT et al., "In vivo near-infrared spectroscopy of rat skin tissue with varying blood glucose levels," Analytical Chemistry 78, pp. 215-223 (2006).
Ye K et al., "Genetic engineering of an allosterically based glucose indicator protein for continuous glucose monitoring by fluorescence resonance energy transfer," Analytical Chemistry, 2003, 75(14), 3451-3459.
Fillat C et al., Suicide gene therapy mediated by the herpes simplex virus.
Scognamiglio V et al., "Protein-based biosensors for diabetic patients," Journal of Fluorescence, 14(5), 491-498 (Sep. 2004).
Moschou E et al., "Fluorescence glucose detection: Advances toward the ideal in vivo biosensor," Journal of Fluorescence, 14(5), 535-547 (Sep. 2004).
Reszka R et al., "Liposome-mediated suicide gene therapy in humans," Methods in Enzymology, 391, 200-208 (2005).
Deuschle K et al., "Construction and optimization of a family of genetically encoded metabolite sensors by semirational protein engineering," Protein Sci. 14: 2304-2314 (2005).
Yonzon CR et al., "A glucose biosensor based on surface-enhanced Raman scattering: Improved partition layer, temporal stability, reversibility, and resistance to serum protein interference," Anal. Chem., 76 (1), pp. 78-85 2004.
Liua L et al., "Glucose permeable poly (dimethyl siloxane) poly (N-isopropyl acrylamide) interpenetrating networks as ophthalmic biomaterials," Biomaterials vol. 26, Issue 3 pp. 233-244 (2005).
Yokota M et al., "A compact polarimetric glucose sensor using a high-performance fibre-optic Faraday rotator," Meas. Sci. Technol. 15 pp. 143-147 (2004).
McNichols J et al., "Development of a non-invasive polarimetric glucose sensor," IEEE-LEOS Newsletter, 12:30-31 (1998).
Olesberg JT, "Noninvasive blood glucose monitoring in the 2.0-2.5 μm wavelength range," Lasers and Electro-Optics Society. LEOS 2001. The 14th Annual Meeting of the IEEE. vol. 2, p. 529.
Dvir D et al., "Non invasive blood glucose monitoring in the critically ill patients," European Society for Clinical Nutrition and Metabolism Congress, Istanbul (2006)—an abstract.
Koo TW et al., "Measurement of glucose in human blood serum using Raman spectroscopy", IEEE-LEOS Newsletter 12(2) 18 (1998).
Amir O et al., "Accurate home and clinical use of a non-invasive continuous glucose monitor," (2006)—an abstract.
H.P. Bennetto, "Electricity generation by microorganisms", Biotech. Educ. vol. 1, No. 4, pp. 163-168, 1990.

(56) References Cited

OTHER PUBLICATIONS

K. Yamada, et al., "Measurement of glucose uptake and intracellular calcium concentration in single, living pancreatic β-cells", The Journal of Biological Chemistry, vol. 275, No. 29, Jul. 2000, pp. 22278-22283.
P. Turkewitsch, "The synthesis of fluorescent chemosensors responsive to cAMP and other nucleotides", Montreal Quebec, Sep. 1998.
G. Gilardi, et al., "Spectroscopic properties of an engineered maltose binding protein", Protein Engineering vol. 10 No. 5, pp. 479-486, 1997.
Hellinga Homme W.et al., "Protein engineering and the development of generic biosensors", TIBTECH Apr. 1998, vol. 16.
Higson S.P.J. et al., "Biosensors: a viable monitoring technology?", Med. & Biol. Eng. & Comput., 1994, 32, 601-609.
Tolosa Leah et al., "Optical assay for glucose based on the luminescnence decay time of the long wavelength dye Cy5™", Sensors and Actuators B 45 (1997) 93-99.
Tolosa Leah et al., "Glucose sensor for low-cost lifetime-based sensing using a genetically engineered protein", Analytical Biochemistry 267, 114-120 (1999).
J.C. Pickup, et al., "Fluorescence-based glucose sensors", Biosensors and Bioelectronics 20 (2005) 2555-2565.
Sakurada M et al., "Relation between glucose-stimulated insulin secretion and intracellular calcium accumulation studied with a superfusion system of a glucose-responsive pancreatic β-cell line MIN6", Endo. 1993, vol. 132, No. 6.
Tsujimura, et al., "Photosynthetic bioelectrochemical cell utilizing cyanobacteria and water-generating oxidase", Enzyme and Microbial Tech. 29 (2001) 225-231.
Deuschle, et al., "Genetically encoded sensors for metabolities", Cytometry A. Mar. 2005;64(1):3-9.
Serganova, et al., "Reporter gene imaging: potential impact on therapy", Nucl Med Biol. Oct. 2005;32(7):763-80.
Laxman, et al., "Noninvasive real-time imaging of apoptosis", Proc Natl Acad Sci USA Dec. 24, 2002;99(26):16551-5.
Fehr, et al., "In vivo imaging of the dynamics of glucose uptake in the cytosol of COS-7 cells by fluorescent nanosensors", J Biol Chem. May 23, 2003; 278(21):19127-33.
Fehr, et al., "Minimally invasive dynamic imaging of ions and metabolites in living cells", Curr Opin Plant Biol. Jun. 2004;7(3):345-51.
Philippe et al., "Vaginal ligature of uterine arteries during postpartum hemorrhage", International Journal of Gynecology & Obstetrics 56 (1997) 267-270.
Tolosa Leah et al., "Lifetime-based sensing of glucose using energy transfer with a long lifetime donor", Analytical Biochemistry 250, 102-108, 1997.
Pickup, et al., "In vivo glucose monitoring: the clinical reality and the promise", Biosens Bioelectron. Apr. 15, 2005;20(10):1897-902.
Olesberg JT et al., "Optical microsensor for continuous glucose measurements in interstitial fluid," Optical Diagnostics and Sensing VI, Proc. of SPIE vol. 6094, 609403, pp. 1605-7422 (2006).
Amir O et al., "Highly accurate non-invasive continuous glucose monitoring in clinical and home use settings," American Diabetes Association, 66th Scientific Session, Washington, D.C. (2006)—an abstract.
Patounakis G., et al., "Active CMOS array sensor for time-resolved fluorescence detection", IEEE Journal of Solid-State Circuits, vol. 41, No. 11, Nov. 2006.
Primack H, "Non-invasive sensing of glucose and hemoglobin," Optical Imaging (2006)—an abstract.
Ackland-Berglund, C et al., "Efficacy of tetracycline-controlled gene expression is influenced by cell type," BioTechniques 18, 196-200 (1995).
Amir O et al., "Evaluation of a non-invasive continuous glucose monitoring device in a home use setting," European Association for the Study of Diabetes, 42nd Annual Meeting, Copenhagen-Malmoe, Denmark-Sweden (2006)—an abstract.
Cote GL "Noninvasive and minimally-invasive optical monitoring technologies," The Journal of Nutrition 131:1596S-1604S (2001).
Berrebi A et al., "A non-invasive evaluation of hematocrit with a new optical sensor," European Hematology Association, 11th Congress, Amstaerdam (2006).
Kononenko A et al., "Evaluation of a non-invasive blood glucose monitoring device for critically ill patients," 26th International Symposium on Intensive Care and Emergency Medicine, Brussels (2006).
Marvin, et al., "The rational design of allosteric interactions in a monomeric protein and its applications to the construction of biosensors", Proc. Natl. Acad. Sci. USA vol. 94, pp. 4366-4371, Apr. 1997.
Communication dated Aug. 29, 2012 which issued during the prosecution of European Patent Application No. 05758905.3.
Written Opinion dated Nov. 23, 2007 which issued during the prosecution of Applicant's PCT/IL2007/000399.
An Office Action dated Aug. 26, 2014, which issued during the prosecution of U.S. Appl. No. 13/173,831.
An Office Action dated Oct. 7, 2013, which issued during the prosecution of U.S. Appl. No. 13/173,831.
U.S. Appl. No. 60/786,532, filed Mar. 28, 2006.
Jadlowiec J et al., "Bone tissue engineering: Recent advances and promising therapeutic agents", Expert opinion on Biological therapy Jan. 2003.
An Office Action dated Jan. 10, 2013 which issued during the prosecution of U.S. Appl. No. 12/225,749.
An Office Action dated Dec. 6, 2012, which issued during the prosecution of U.S. Appl. No. 12/064,946.
Notice of Allowance dated Mar. 20, 2013, which issued during the prosecution of U.S. Appl. No. 12/064,946.
An Office Action dated May 14, 2012, which issued during the prosecution of U.S. Appl. No. 12/515,818.
Stagner, et al., "The pancreas as an islet transplantation site", Sep. 1, 2007, Journal of the Pancreas, vol. 8, No. 5, pp. 628-636.
T. Yagishita, S. Sawayama, K.-I. Tsukahara, and T. Ogi, "Effects of intensity of incident light and concentrations of Synechococcus sp. and 2-hydroxy-1,4-naphthoquinone on the current output of photosynthetic electrochemical cell," Solar Energy, vol. 61, No. 5, pp. 347-353, 1997. Abstract.
T. Yagishita, S. Sawayama, K.-I. Tsukahara, and T. Ogi, "Performance of photosynthetic celectrochemical cells using immobilized Anabaena variabilis M-3 in discharge/culture cycles," J. Ferment. Bioeng., vol. 85, No. 5, pp. 546-549, 1998. Abstract.
A. Solovev, E. Y. Katz, V. A. Shuvalov, and Y. E. Erokhin, "Photoelectrochemical effects for chemicall modified platinum electrodes with immobilized reaction centers from Rhodobacter sphaerides R-26," Bioelectrochem. Bioenerg., vol. 26, pp. 29-41, 1991. Abstract.
E. Y. Katz, and A. A. Solovev, "Photobioelectrodes on the basis of photosynthetic reaction centers. Study of exogenous quinines as possible electron transfer mediators," Anal. Chim. Acta., vol. 266, pp. 97-106, 1992. Abstract.
A. Halme, X. Zhang and N. Rintala, "Monitoring and control of a bacteria fuel cell process by colour analysis," in Proc. 7th Int. Conf. Computer Applications on Biotechnology, Osaka, Japan, May 31-Jun. 4, 1998, pp. 467-462.
An International Search Report dated Apr. 17, 2001, which issued during the prosecution of Applicant's PCT/IL01/00031.
An International Preliminary Report on Patentability dated Jul. 12, 2003, which issued during the prosecutio of Applicant's PCT/IL01/00031.
A Restriction Requirement dated Nov. 2, 2006, which issued during the prosecution of U.S. Appl. No. 10/466,069.
An International Search Report and a Written Opinion both dated Jun. 9, 2010, which issued during the prosecution of Applicant's PCT/IL2009/001114.
An International Preliminary Report on Patentability dated May 31, 2011, which issued during the prosecution of Applicant's PCT/IL2009/001114.
An English Translation of an Office Action dated Dec. 8, 2011, which issued during the prosecution of Chinese Patent Application No. 200580047325.4.
An Office Action dated Jan. 23, 2009, which issued during the prosecution of U.S. Appl. No. 10/466,069.

(56) References Cited

OTHER PUBLICATIONS

An Office Action dated Jun. 22, 2010, which issued during the prosecution of U.S. Appl. No. 10/466,069.
Notice of Allowance dated Oct. 28, 2010, which issued during the prosecution of U.S. Appl. No. 10/466,069.
An International Search Report and a Written Opinion both dated Oct. 1, 2008, which issued during the prosecution of Applicant's PCT/IL2007/001471.
An International Preliminary Report on Patentability dated Jun. 3, 2009, which issued during the prosecution of Applicant's PCT/IL2007/001471.
An International Search Report and a Written Opinion both dated May 11, 2006, which issued during the prosecution of Applicant's PCT/IL2005/001262.
An International Preliminary Report on Patentability dated Jun. 5, 2007, which issued during the prosecution of Applicant's PCT/IL2005/001262.
Partial International Search Report dated Mar. 24, 2014, which issued during the prosecution of Applicant's PCT/IB2013/061368.
An International Search Report and a Written Opinion both dated Jun. 12, 2014, which issued during the prosecution of Applicant's PCT/IB2013/061368.
An Office Action dated Aug. 26, 2013, which issued during the prosecution of U.S. Appl. No. 12/344,103.
An English Translation of an Office Action dated Mar. 3, 2014, which issued during the prosecution of Chinese Patent Application No. 200980157599.7.
An English Translation of an Office Action dated Mar. 10, 2014, which issued during the prosecution of Chinese Patent Application No. 200980157599.7.
European Search Report dated Apr. 15, 2013, which issued during the prosecution of Applicant's European App No. 09834227.2.
Communication dated Feb. 26, 2013, which issued during the prosecution of EP Patent Application No. 07736139.2.
An International Search Report and a Written Opinion both dated Nov. 21, 2012, which issued during the prosecution of Applicant's PCT/IL2012/000268.
An English Translation of an Office Action dated Apr. 1, 2013 which issued during the prosecution of Chinese Patent Application No. 200980157599.
A European Search Report and communication dated Oct. 31, 2012, which issued during the prosecution of EP Patent Application No. 12 15 9273.
U.S. Appl. No. 62/258,783, filed Nov. 23, 2015.
An International Search Report and a Written Opinion both dated Apr. 1, 2016, which issued during the prosecution of Applicant's PCT/IL2015/051022.
An Office Action dated Jul. 2, 2014, which issued during the prosecution of U.S. Appl. No. 13/141,936.
An Office Action dated Jan. 22, 2015, which issued during the prosecution of U.S. Appl. No. 13/141,936.
An Office Action dated Aug. 26, 2013, which issued during the prosecution of U.S. Appl. No. 13/141,936.
Wu H et al., in "In situ electrochemical oxygen generation with an immunoisolation device," Ann N Y Acad Sci 875:105-25 (1999).
Khamsi R, , "Microbes Pass Valuable Gas," Wired News, May 20, 2003.
Parikh et al., "Role of Spirulina in the control of glycemia and lipidemia in type 2 diabetes mellitus," J Med Food 2001, Winter 4(4): 193-199.
Katz E et al., "Biochemical fuel cells," Chapter 21 of Handbook of Fuel Cells—Fundamentals, Technology and Applications, Vielstich W et al, eds., vol. 1: Fundamentals and Survey of Systems, John Wiley & Sons (2003).
Haselkorn A, "Microbial fuel cells to power future: new design promises medical breakthroughs," The Daily Californian Online, Aug. 28, 2002.
Pescovitz D, "Body battery," Lab Notes—Research from the College of Engineering, University of California, Berkeley, vol. 2, Issue 6 (Aug. 2002).

K. B. Lam, E. Johnson, and L. Lin, "A Bio-Solar Cell Powered by Sub-Cellular Plant Photosystems," in Proc. IEEE Conf. on Micro Electro Mechanical Syst.(MEMS 2004), Maastricht, The Netherlands, Jan. 25-29, 2004, pp. 220-223.Abstract.
E. Y, Katz, A. Y. Shkuropatov, and V. A. Shuvalov, "Electrochemical approach to the development of a photoelectrode on the basis of photosynthetic reaction centers," Bioelectrochem. Bioenerg., vol. 23, pp. 239-247, 1990. Abstract.
N. Mano, F. Mao, and A. Heller, "Characteristics of a miniature compartment-less glucose-O2 biofuel cell and its operation in a living plant," J. Am. Chem. Soc., vol. 125, No. 21, pp. 6588-6594, 2003. Abstract.
M. Chiao, K. B. Lam, Y.-C. Su, and L. Lin, "A Miniaturized Microbial Fuel Cell," Technical Digest of Solid-State Sensors and Actuators Workshop, Hilton Head Island, Jun. 2002, pp. 59-60.
M. Chiao, K. B. Lam, and L. Lin, "A microfabricated microbial fuel cell," in Proc. IEEE Conf. on Micro Electro Mechanical Syst. (MEMS 2003), Kyoto, Japan, Jan. 19-23, 2003, pp. 383-386. Abstract.
E. Y. Katz, A. Y. Shkuropatov, O. I. Vagabova, and V. A. Shuvalov, "Coupling of photoinduced charge separation in reaction centers of photosynthetic bacteria with electron-transfer to a chemically modified electrode," Biochima et Biophysica Acta., vol. 976, pp. 121-128, 1989.
X. Zhang and A. Halme, "Modelling of a microbial fuel cell process," Biotechnology Letters, vol. 17, No. 8, pp. 809-814, 1995. Abstract.
Lam KB et al, "A micro photosynthetic electrochemical cell," Micro Electro Mechanical Systems, 2003. MEMS-03 Kyoto. IEEE The Sixteenth Annual International Conference on, pp. 391- 394 (ISSN: 1084-6999) (Jan. 19-23, 2003). Abstract.
T. Yagishita, T. Horigome, "Effects of light, CO2, and inhibitors on the current output of biofuel cells containing the photosynthetic organism *Synechococcus* sp.," J. Chem. Tech. Biotech, vol. 56, No. 4, pp. 393-399, 1993. Abstract.
T. Yagishita, T. Horigome, K. Tanaka, "Biofuel-cells containing photosynthetic microorganisms," J. Electrochem. Soc. Japan, vol. 61, No. 6, pp. 687-688, 1993. Abstract.
T. Yagishita, S. Sawayama, K.-I. Tsukahara, and T. Ogi, "Effects of glucose addition and light on current outputs in photosynthetic electrochemical cells using *Synechocystis* sp. PCC6714," J. Biosci. Bioeng., vol. 99, No. 2, pp. 210-214, 1999 Abstract.
R. M. Allen and H. P. Bennetto, "Microbial fuel cells: electricity production from carbohydrates," Appl. Biochem. Biotech., vol. 39/40, pp. 27-40, 1993. Abstract.
Notice of Allowance dated Jan. 20, 2011, which issued during the prosecution of U.S. Appl. No. 11/632,587.
An Office Action dated Nov. 28, 2012, which issued during the prosecution of U.S. Appl. No. 12/064,946.
An Office Action dated Apr. 24, 2012, which issued during the prosecution of U.S. Appl. No. 12/064,946.
An Office Action dated Jul. 26, 2012, which issued during the prosecution of European Patent Application No. 05812146.
A Supplementary European Search Report dated Jun. 20, 2012, which issued during the prosecution of Applicant's European Patent Application No. 05812146.
An International Search Report and a Written Opinion both dated Oct. 1, 2008, which issued during the prosecution of Applicant's PCT/IL2007/001447.
An International Search Report and a Written Opinion both dated Jan. 25, 2012, which issued during the prosecution of Applicant's PCT/IL2011/000445.
An English Translation of an Office Action dated Mar. 2, 2012, which issued during the prosecution of Japanese Patent Application No. 2007-544006.
An English Translation of an Office Action dated May 31, 2011, which issued during the prosecution of Japanese Patent Application No. 2007-544006.
Yun Jung Heo et al., "Towards Smart Tattoos: Implantable Biosensors for Continuous Glucose Monitoring" Adv. Healthcare Mater. 2013, 2, 43-56.

(56) References Cited

OTHER PUBLICATIONS

Beningo et al. Double-Hydrogel Substrate As a Model System for Three-Dimensional Cell Culture; Methods in Cell Biology, vol. 370; Adhesion Protein Protocols, 2nd Ed. (2007) pp. 203-211.
An International Search Report and a Written Opinion both dated Jan. 25, 2010, which issued during the prosecution of Applicant's PCT/IL2009/000905.
An Office Action dated May 14, 2010, which issued during the prosecution of U.S. Appl. No. 12/315,102.
An Office Action dated Jan. 7, 2011, which issued during the prosecution of U.S. Appl. No. 11/001,556.
Faithful, N. S. Anaesthesia, 42, pp. 234-242 (1987).
Lacy PE et al., "Maintenance of normoglycemia in diabetic mice by subcutaneous xenografts of encapsulated islets," Science 1782-4 (1991).
T. Akiba, H. P. Bennetto, J. L. Stirling, and K. Tanaka, "Electricity production from alkalophilic organisms," Biotechnol., vol. 9, No. 9, 611-616, 1987. Abstract.
Kaisers U et al., "Liquid ventilation," British Journal of Anaesthesia 91 (1) : 143-151 (2003).
Steve Barash et al., "Human secretory signal peptide description by hidden Markov model and generation of a strong artificial signal peptide for secreted protein expression", Biochemical and Biophysical Research Communications 294 (May 15, 2002) 835-842.
"Membrane.", Merriam-Webster.com. Merriam-Webster, n.d. Web. Sep. 29, 2016.
An Office Action dated Jun. 11, 2015, which issued during the prosecution of U.S. Appl. No. 12/225,749.
An Office Action dated Dec. 9, 2014, which issued during the prosecution of U.S. Appl. No. 12/225,749.
An Office Action dated Sep. 7, 2007, which issued during the prosecution of U.S. Appl. No. 10/466,069.
A Notice of Allowance dated Jun. 10, 2013, which issued during the prosecution of U.S. Appl. No. 13/356,053.
Partial International Search Report dated May 27, 2015, which issued during the prosecution of Applicant's PCT/IB2015/051427.
An Office Action dated Jun. 17, 2014, which issued during the prosecution of U.S. Appl. No. 13/089,096.
An Office Action dated Mar. 13, 2015, which issued during the prosecution of U.S. Appl. No. 13/089,096.
An Office Action dated Oct. 23, 2014, which issued during the prosecution of U.S. Appl. No. 13/089,096.
—Jithesh V. Veetil et al. "A Glucose Sensor Protein for Continuous Glucose Monitoring" Biosens Bioelectron. Dec. 15, 2010; 26(4): 1650-1655. doi:10.1016/j.bios.2010.08.052.
Jonghoon Choi et al: "Interactions between mesenchymal stem cells and T cells on a single cell level a nanowell array", Nano/Molecular Medicine and Engineering (NANOMED), 2012 IEEE 6th International Conference on, IEEE, Nov. 4, 2012 (Nov. 4, 2012), pp. 111-116.
An International Search Report and a Written Opinion both dated Aug. 3, 2015, which issued during the prosecution of Applicant's PCT/IB2015/051427.
European Search Report dated Sep. 9, 2014 which issued during the prosecution of Applicant's European App No. 05758905.3.
Sha Jin et al., "Construction of a Panel of Glucose Indicator Proteins for Continuous Glucose Monitoring", Biosens Bioelectron. Apr. 15, 2011; 26(8): 3427-3431. doi:10.1016/j.bios.2011.01.017.
L. Leheninger, Biochemistry, Worth Publishers, Inc. 1978, Chapter 14, pp. 363-364.
Smith AJ, "Acetate assimilation by nitrobacter agilis in relation to its 'obligate autotrophy' ", Journal of Bacteriology 95:844 (1968).
Silva AI et al., "An overview on the development of a bio-artificial pancreas as a treatment of insulin- dependent diabetes mellitus," Med Res Rev 26 (2) : 181-222 (2006).
Notice of Allowance dated Jan. 21, 2015, which issued during the prosecution of U.S. Appl. No. 13/173,831.
An Office Action dated Aug. 31, 2010, which issued during the prosecution of U.S. Appl. No. 11/632,587.

Communication from the European Patent Office dated May 8, 2015, which issued during the prosecution of European Patent Application No. 05758905.3.
An Office Action dated Jan. 29, 2016, which issued during the prosecution of U.S. Appl. No. 12/225,749.
An Invitation to pay additional fees dated Jan. 19, 2016, which issued during the prosecution of Applicant's PCT/IL2015/051022.
An Office Action dated Mar. 2, 2017, which issued during the prosecution of U.S. Appl. No. 14/758,493.
An Office Action dated Feb. 16, 2017, which issued during the prosecution of Chinese Patent Application No. 201380073934.1.
Pieper et al. Preparation and Characterization of Porous Crosslinked Collagenous Matrices Containing Bioavailable Chondroitin Sulphate; Biomaterials, vol. 20 (1999) pp. 847-858.
Ye et al. Studies on the Use of Hollow Fibre Membrane Bioreactors for Tissue Generation by Using Rat Bone Marrow Fibroblastic Cells and a Composite Scaffold; Journal of Material Science, Material in Medicine, vol. 18 (2007) pp. 641-648.
Kovacic et al. New Insights Into Cytosolic Glucose Levels During Differentiation of 3T3-L1 Fibroblasts Into Adipocytes; The Journal of Biological Chemistry, vol. 286, No. 15 (2011) pp. 13370-13381.
Khodjakov et al. Imaging the Division Process in Living Tissue Culture Cells; Methods, vol. 38, No. 1 (2006) pp. 1-24.
Fischer et al. Stiffness-Controlled Three-Dimensional Extracellular Matrices for High-Resolution Imaging of Cell Behavior; Nature Protocols, vol. 7, No. 11 (10/252012) pp. 2056-2066.
An Office Action dated Oct. 5, 2016, which issued during the prosecution of U.S. Appl. No. 14/758,493.
Beningo KA et al., "Flexible Polyacrylamide Substrata for the Analysis of Mechanical Interactions at CellSubstratum Adhesions," in Methods in Cell Biology, vol. 69 (2002), pp. 325-339.
Whitford et al. Interest in Hollow-Fiber Perfusion Bioreactors Is Growing; BioProcess International, Oct. 2009, pp. 54-63.
An International Preliminary Report on Patentability dated Jun. 30, 2015, which issued during the prosecution of Applicant's PCT/IB2013/061368.
An International Preliminary Report on Patentability dated Aug. 30, 2016, which issued during the prosecution of Applicant's PCT/IB2015/051427.
An International Preliminary Report on Patentability dated Jan. 7, 2014, which issued during the prosecution of Applicant's PCT/IL2012/000268.
An Office Action dated Jun. 7, 2016, which issued during the prosecution of U.S. Appl. No. 14/758,493.
Vyas NK et al., "Sugar and Signal-Transducer Binding Sites of the *Escherichia-Coli* Galactose Chemoreceptor Protein," 1988, Science (Washington DC) , vol. 242, Nr. 4883, pp. 1290-1295.
Senseonics-EASD-Poster2 (Oct. 2012).
Steinmeyer R et al., "Improved Fluorescent Proteins for Single-Molecule Research in Molecular Tracking and Co-Localization," Journal of Fluorescence, vol. 15, No. 5, Sep. 2005.
U.S. Appl. No. 62/063,211, filed Oct. 13, 2014.
An International Search Report and a Written Opinion both dated Sep. 13, 2017, which issued during the prosecution of Applicant's PCT/IL2017/050456.
Communication dated Dec. 13, 2016, which issued during the prosecution of European Patent Application No. 13821988.6.
European Search Report dated May 7, 2018, which issued during the prosecution of Applicant's European App No. 15787690.
An International Preliminary Report on Patentability dated Oct. 23, 2018, which issued during the prosecution of Applicant's PCT/IL2017/050456.
An International Preliminary Report on Patentability dated May 31, 2016, which issued during the prosecution of Applicant's PCT/IL2015/051022.
An Office Action dated Jan. 31, 2018, which issued during the prosecution of Indian Patent Application No. 9075/DELNP/2008.
Joseph et al., Pressure Sensitive Adhesives with Porosity. PSTCTech Papers, published online May 31, 2010, http://www.pstc.org/files/public/TECH33Papers/2010JosephEugene.pdf, pp. 106 (Year: 2010).
Ross et al., Synthetic substrates for long-term stem cell culture. Polymer, vol. 53, Issue 13, Jun. 7, 2012, pp. 2533-2539. (Year: 2012).

(56) References Cited

OTHER PUBLICATIONS

An Office Action dated May 4, 2018, which issued during the prosecution of U.S. Appl. No. 15/360,523.
An Office Action dated Jan. 12, 2018, which issued during the prosecution of Chinese Patent Application No. 201380073934.1.
An Office Action dated Mar. 9, 2018, which issued during the prosecution of U.S. Appl. No. 14/881,431.
U.S. Appl. No. 62/325,136, filed Apr. 20, 2016.
Communication from the Examining Division dated Apr. 9, 2020 which issued during the prosecution of Applicant's European App No. 17724121.3.
Wikipedia—Proteinogenic amino acid, last edited Jun. 13, 2020.
LibreTexts Biology—3.3B: Amino Acids (002), Jun. 16, 2020.
Sigma-Aldrich Amino Acid Reference Charts (002).
Communication Art. 94(3), EPC (002), Appln. No. 17 724 121.3-1118, dated Apr. 9, 2020.

* cited by examiner

FRET-BASED GLUCOSE-DETECTION MOLECULES

CROSS REFERENCE TO RELATED APPLICATIONS

The present patent application is the US National Phase of International Patent Application PCT/IL2017/050456 to Biron-Sorek et al., filed Apr. 19, 2017, entitled "FRET-BASED GLUCOSE-DETECTION MOLECULES," which published as WO 2017/183030, and which claims priority to U.S. provisional patent application 62/325,136 to Biron-Sorek et al., filed Apr. 20, 2016, and entitled "FRET-BASED GLUCOSE-DETECTION MOLECULES," which is incorporated herein by reference.

FIELD OF THE INVENTION

Some applications of the present invention relate generally to sensor molecules for detecting an analyte in a body. More specifically, some applications of the present invention relate to sensor molecules that provide an optical signal that is indicative of detection of the analyte.

BACKGROUND

The monitoring of various medical conditions often requires measuring the levels of various components within the blood. In order to avoid invasive repeated blood drawing, implantable sensors aimed at detecting various components of blood in the body have been developed. More specifically, in the field of endocrinology, in order to avoid repeated "finger-sticks" for drawing blood to assess the concentrations of glucose in the blood in patients with diabetes mellitus, implantable glucose sensors have been discussed.

One method for sensing the concentration of an analyte such as glucose relies on Forster Resonance Energy Transfer (FRET). FRET involves the transfer of energy from an excited fluorophore (the donor) to another fluorophore (the acceptor) when the donor and acceptor are in close proximity to each other, leading to light emission by the acceptor. (F clarity and correctness, this FRET-based emission is not referred to herein as fluorescence.) Because of the high sensitivity of the FRET signal to the relative proximity of the fluorophores it is often used in biological research as a measurement tool. For example, the concentration of an analyte such as glucose can be measured by creating a fused sensor which includes two fluorophores and a third moiety which has specific binding site for the analyte. The conformational change of the fused sensor which results from the binding of the analyte changes the distance between the fluorophores, affecting the FRET signal and thus enabling the measurement of the analyte concentration.

PCT Patent Application Publication WO 2006/006166 to Gross et al., which is incorporated herein by reference, describes a protein which includes a glucose binding site, cyan fluorescent protein (CFP), and yellow fluorescent protein (YFP). The protein is configured such that binding of glucose to the glucose binding site causes a reduction in a distance between the CFP and the YFP. Apparatus is described for detecting a concentration of a substance in a subject, the apparatus comprising a housing adapted to be implanted in the subject. The housing comprises a Forster resonance energy transfer (FRET) measurement device and cells genetically engineered to produce, in situ, a FRET protein having a FRET complex comprising a fluorescent protein donor, a fluorescent protein acceptor, and a binding site for the substance.

An alternative approach to glucose sensing has been discussed e.g. by Y J Heo et al., in "Towards Smart Tattoos: Implantable Biosensors for Continuous Glucose Monitoring," Adv. Healthcare Mater. 2013 January; 2(1):43-56 (Epub Nov. 26, 2012). Heo et al. provide a review of the efforts to develop analyte monitoring methods, which include placing a fluorescent material sensitive to a target analyte, e.g., glucose, under the skin and reading the optical signal through the skin, thus enabling measurement of the analyte.

In recent years, improved far-red fluorophores, having a significant portion of their emission spectrum above 650 nm, have been developed in order to exploit optical properties of biological tissue and enable in-vivo deep imaging, including, e.g., TagRFP, mRuby, mRuby2, mPlum, FusionRed, mNeptune, mNeptune2.5, mCardinal, Katushka, mKate, mKate2, mRaspberry and others. The relative emission of these fluorophores at an optical window above 650 nm is typically 10-50%, enabling sufficiently-effective detection through the skin. Additionally, infrared phytochromes such as iRFP, IFP1.4, and IFP2.0 have been developed which further push the emission spectrum into the infrared; however, these phytochromes depend on the availability of biliverdin, possibly complicating their practical use. Red fluorophores may effectively be used in conjunction with shorter-wavelengths fluorophores (e.g., green) to create FRET couples that can be used to develop different types of biosensors, as shown for example by Lam et al.

SUMMARY OF THE INVENTION

FRET-based glucose-detection molecules are described. Each molecule provides a FRET-based signal that is indicative of glucose concentration, and is sensitive within physiologically-relevant ranges and temperatures.

There is therefore provided, in accordance with an application of the present invention, a protein having a glucose-binding site, the protein having SEQ ID No. 1.

There is further provided, in accordance with an application of the present invention, a protein having a glucose-binding site, the protein having SEQ ID No. 2.

There is further provided, in accordance with an application of the present invention, a protein having a glucose-binding site, the protein having SEQ ID No. 3.

There is further provided, in accordance with an application of the present invention, a protein having a glucose-binding site, the protein having SEQ ID No. 4.

There is further provided, in accordance with an application of the present invention, a protein having a glucose-binding site, the protein having SEQ ID No. 5.

There is further provided, in accordance with an application of the present invention, a protein having a glucose-binding site, the protein having SEQ ID No. 6.

There is further provided, in accordance with an application of the present invention, a protein having a glucose-binding site, the protein including an amino acid chain, the amino acid chain including an amino acid sequence greater than 98 percent identical to SEQ ID No. 9, and residue 16 of SEQ ID No. 9 is disposed at the glucose-binding site, and is a hydrophilic amino acid.

In an application, the amino acid sequence is SEQ ID No. 9.

In an application, amino acid 16 of SEQ ID No. 9 is a polar amino acid.

In an application, amino acid 16 of SEQ ID No. 9 is an uncharged polar amino acid.

In an application, amino acid 16 of SEQ ID No. 9 is Gln.

In an application, amino acid 16 of SEQ ID No. 9 is Asn.

In an application, amino acid 16 of SEQ ID No. 9 is an amidic amino acid.

In an application, amino acid 16 of SEQ ID No. 9 is Gln.

In an application, amino acid 16 of SEQ ID No. 9 is Asn.

In an application:
the amino acid sequence is a first amino acid sequence,
the amino acid chain further includes a second amino acid sequence that is greater than 98 percent identical to SEQ ID No. 11, and
the first amino acid sequence is closer to an N-terminal end of the protein than is the second amino acid sequence.

In an application, the N-terminal end of the second amino acid sequence begins immediately after the C-terminal end of the first amino acid sequence.

In an application, the amino acid chain further includes a fluorophore amino acid sequence that defines a fluorophore and is disposed between the C-terminal end of the first amino acid sequence and the N-terminal end of the second amino acid sequence.

In an application, the fluorophore amino acid sequence is a donor-fluorophore amino acid sequence, and defines a donor fluorophore.

In an application, the amino acid chain further includes an acceptor-fluorophore amino acid sequence that defines an acceptor fluorophore, and:
the first amino acid sequence is between the donor-fluorophore amino acid sequence and the acceptor-fluorophore amino acid sequence, and
the acceptor fluorophore is excitable by the donor fluorophore by Förster Resonance Energy Transfer (FRET).

In an application, the amino acid chain further includes a linker sequence that connects the acceptor-fluorophore amino acid sequence to the first sequence, and has SEQ ID No. 8.

There is further provided, in accordance with an application of the present invention, a protein having a glucose-binding site, the protein including an amino acid chain, the amino acid chain including an amino acid sequence greater than 98 percent identical to SEQ ID No. 9, and residue 16 of SEQ ID No. 9 is disposed at the glucose-binding site, and is Val.

There is further provided, in accordance with an application of the present invention, a protein having a glucose-binding domain, the protein including an amino acid chain, the amino acid chain including, in order: SEQ ID No. 7; SEQ ID No. 9; SEQ ID No. 10; and SEQ ID No. 11.

In an application, the amino acid chain further includes a Val-Ser-Lys sequence before SEQ ID No. 7.

In an application, the amino acid chain further includes SEQ ID No. 8 between SEQ ID No. 7 and SEQ ID No. 9.

In an application, the amino acid chain further includes a Ser-Lys sequence between SEQ ID No. 9 and SEQ ID No. 10.

In an application, the amino acid chain further includes a Met-Val sequence between SEQ ID No. 9 and the Ser-Lys sequence.

In an application, the amino acid chain further includes a Glu-Leu sequence between SEQ ID No. 10 and SEQ ID No. 11.

In an application, the amino acid chain further includes a Tyr-Lys sequence between the Glu-Leu sequence and SEQ ID No. 11.

There is further provided, in accordance with an application of the present invention, a protein having a glucose-binding domain, the protein including an amino acid chain, the amino acid chain including, in order:
optionally, a Val-Ser-Lys sequence;
SEQ ID No. 7;
optionally, SEQ ID No. 8;
SEQ ID No. 9;
optionally, a Met-Val sequence;
optionally, a Ser-Lys sequence;
SEQ ID No. 10;
optionally, a Glu-Leu sequence;
optionally, a Tyr-Lys sequence; and
SEQ ID No. 11.

There is further provided, in accordance with an application of the present invention, a protein having a glucose-binding site, the protein including an amino acid chain, the amino acid chain including:
a donor fluorophore region that has an amino acid sequence that defines a donor fluorophore;
an acceptor fluorophore region that has an amino acid sequence that defines an acceptor fluorophore that is excitable by the donor fluorophore by Förster Resonance Energy Transfer (FRET);
a glucose-binding region that has an amino acid sequence that at least in part defines the glucose-binding site; and
a linker sequence having SEQ ID No. 8 that connects the acceptor fluorophore region to the glucose-binding region.

In an application, the glucose-binding region has SEQ ID No. 9.

In an application, the linker sequence connects a C-terminal end of the amino acid sequence of the acceptor fluorophore region, to an N-terminal end of the amino acid sequence of the glucose-binding region.

In an application, the donor fluorophore is at least 98% identical to Clover.

In an application, the acceptor fluorophore is at least 98% identical to mKate2.

In an application, the acceptor fluorophore is at least 98% identical to mNeptune2.5.

There is further provided, in accordance with an application of the present invention, a protein having a glucose-binding site, the protein including:
a donor fluorophore region that has a donor-fluorophore amino acid sequence that defines a donor fluorophore;
an acceptor fluorophore region that has an acceptor-fluorophore amino acid sequence that defines an acceptor fluorophore that (i) is excitable by the donor fluorophore by Förster Resonance Energy Transfer (FRET), and (ii) has a peak emission wavelength in the red-to-far-red spectrum;
a glucose-binding region that defines the glucose-binding site, the glucose-binding region having a glucose-binding-region amino acid sequence that includes SEQ ID No. 9; and:
the protein has an amino acid sequence in which the glucose-binding-region amino acid sequence is disposed between the donor-fluorophore amino acid sequence and the acceptor-fluorophore amino acid sequence, and the protein is configured to reduce a distance between the first fluorophore region and the second fluorophore region in response to binding of glucose to the glucose-binding site.

In an application, amino acid 16 of SEQ ID No. 9 is Val.

In an application, amino acid 16 of SEQ ID No. 9 is a polar amino acid.

In an application, amino acid 16 of SEQ ID No. 9 is an uncharged polar amino acid.

In an application, amino acid 16 of SEQ ID No. 9 is Gln.

In an application, amino acid 16 of SEQ ID No. 9 is Asn.

In an application, residue 16 of SEQ ID No. 9 is a hydrophilic amino acid.

In an application, amino acid 16 SEQ ID No. 9 is an amidic amino acid.

In an application, amino acid 16 of SEQ ID No. 9 is Gln.

In an application, amino acid 16 of SEQ ID No. 9 is Asn.

The present invention will be more fully understood from the following detailed description of applications thereof, taken together with the drawings, in which:

DETAILED DESCRIPTION OF EMBODIMENTS

Figure 1:
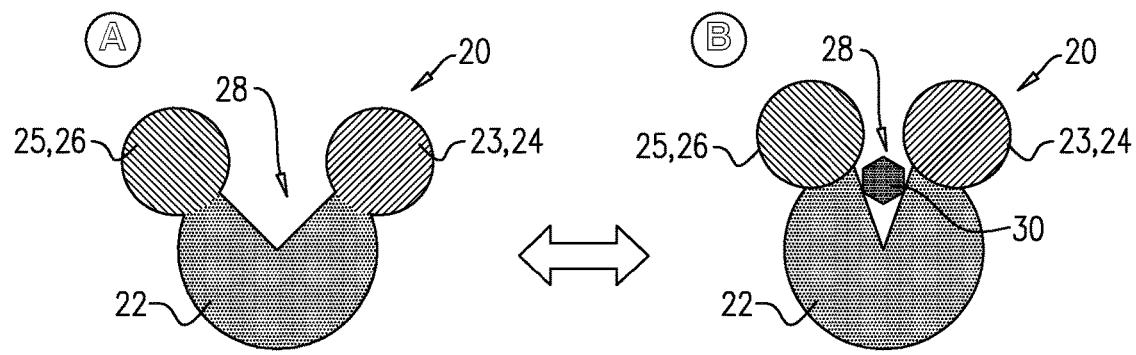
FIG. 1 is a schematic illustration of a generalized FRET-based glucose-detection molecule that represents the FRET-based glucose-detection molecules described herein, in accordance with some applications of the invention.

Reference is made to FIG. 1, which is a schematic illustration of a generalized FRET-based glucose-detection molecule 20 that represents the FRET-based glucose-detection molecules described herein, in accordance with some applications of the invention. Molecule 20 (as may each of the molecules that it represents) may be used in glucose-detecting implants, e.g., implanted subcutaneously in a subject. Molecule 20 (as do each of the molecules that it represents) comprises a glucose-binding region 22, a donor fluorophore region 23 that comprises a donor fluorophore 24, and an acceptor fluorophore region 25 that comprises an acceptor fluorophore 26. Molecule 20 (e.g., glucose-binding region 22) comprises a glucose-binding site 28. In the disassociated state of molecule 20 (state A), fluorophores 24 and 26 are not in a proximity to each other that allows FRET. Binding of a glucose molecule 30 to glucose-binding site 28 results in a conformational change in molecule 20 to its associated state (state B), bringing fluorophores 24 and 26 into a proximity that allows FRET.

A substantial portion (e.g., at least 20 percent, e.g., at least 40 percent, at least 80 percent) and/or the peak of the emission spectrum of acceptor fluorophore 26 is in the red and/or far-red spectrum (e.g., has a wavelength above 620 nm, such as above 650 nm, e.g., 620-850 nm, such as 650-800 nm). This facilitates, for example, the use of the molecules described herein within a subcutaneous implant, and transcutaneous detection of emission from fluorophore 26, e.g., by a skin-mounted detector. For example, the gene encoding any of the FRET-based glucose-detection molecules described herein may be inserted into mammalian cells, e.g., human cells, such as into the AAVS1 locus on chromosome 19, and the cells housed within the subcutaneous implant, such that the cells express the molecule. For some applications, the cells are human Retinal Pigment Epithelial (RPE) cells. For such applications, the gene encoding the molecule typically further comprises a nucleotide sequence that encodes a signal peptide that promotes secretion of the molecule, as is known in the art. (The signal peptide is typically cleaved during or after secretion such that it does not feature in the mature molecule.) For some applications, the signal peptide is SEQ ID No. 12, which is described in Barash et al. (Biochem Biophys Res Commun. 2002 Jun. 21; 294(4):835-42) and whose amino acid sequence is:

MWWRLWWLLLLLLLLWPMVW A       21

For some applications, the molecules described herein are used in combination with devices and techniques described in the following references, which are incorporated herein by reference:

PCT application IL2015/051022 to Brill, which published as WO 2016/059635;

U.S. Pat. No. 7,951,357 to Gross et al.;

US Patent Application Publication 2010/0160749 to Gross et al.;

US Patent Application Publication 2010/0202966 to Gross et al.;

US Patent Application Publication 2011/0251471 to Gross et al.;

US Patent Application Publication 2012/0059232 to Gross et al.;

US Patent Application Publication 2013/0006069 to Gil et al.;

PCT Publication WO 2006/006166 to Gross et al.;

PCT Publication WO 2007/110867 to Gross et al.;

PCT Publication WO 2010/073249 to Gross et al.;

PCT Publication WO 2013/001532 to Gil et al.;

PCT Publication WO 2014/102743 to Brill et al.;

U.S. Provisional Patent Application 60/588,211, filed Jul. 14, 2004;

U.S. Provisional Patent Application 60/658,716, filed Mar. 3, 2005;

U.S. Provisional Patent Application 60/786,532, filed Mar. 27, 2006;

U.S. Provisional Patent Application 61/746,691, filed Dec. 28, 2012; and

U.S. Provisional Patent Application 61/944,936, filed Feb. 26, 2014.

Quantitative detection of FRET-based emission is typically performed (e.g., by a detector unit) by comparing (i) emission from the acceptor fluorophore in response to excitation of the donor fluorophore (i.e., due to FRET), with (ii) emission from the acceptor fluorophore in response to direct excitation of the acceptor fluorophore (which is referred to herein as fluorescence), which serves as a control, e.g., for variations such as distance between the molecule and the detector. The donor fluorophore is excited using light of a particular wavelength range (e.g., 430-520 nm), and direct excitation of the acceptor fluorophore is achieved using light of a different wavelength (e.g., 530-620 nm). The detector may measure (i) and then (ii), or vice versa. The ratio between (i) and (ii) is referred to herein as the "FRET:Fluorescence ratio" ("FRET:F ratio").

For some applications, acceptor fluorophore 26 is (or is based on, e.g., is greater than 98 percent identical to) the "mKate2" fluorophore. For some applications, acceptor fluorophore 26 is (or is based on, e.g., is greater than 98 percent identical to) the "mNeptune2.5" fluorophore. Typically, donor fluorophore 24 is (or is based on, e.g., is greater than 98 percent identical to) the "Clover" fluorophore.

Figure 2:
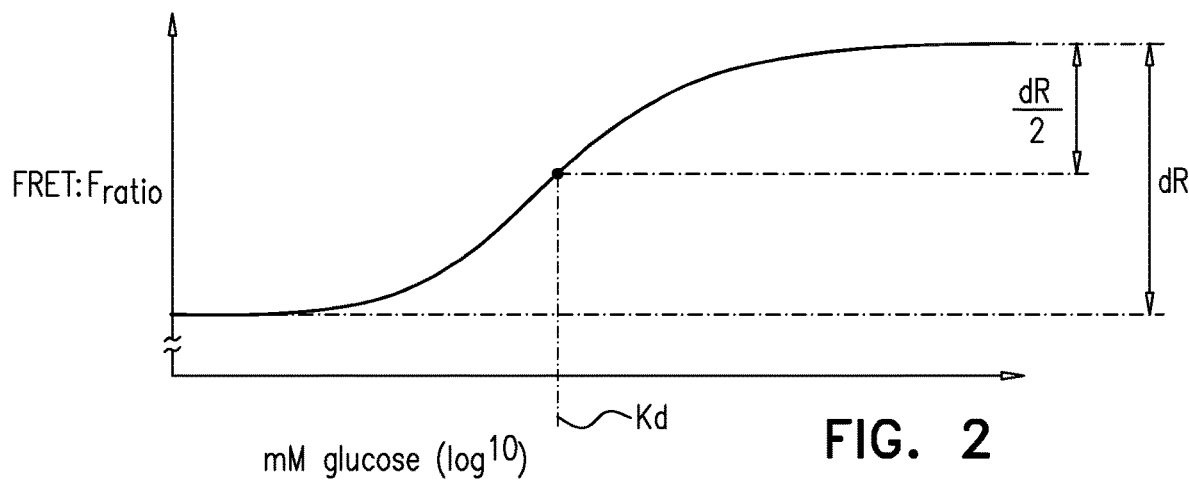
FIG. 2 is a graph that illustrates, in a generalized manner, FRET behavior of the generalized molecule (and of the molecules that it represents), in accordance with some applications of the invention.

Reference is also made to FIG. 2, which is a graph that illustrates, in a generalized manner, FRET behavior of molecule 20 (and of the molecules that it represents), in accordance with some applications of the invention. Three important features of molecules suitable for FRET-based glucose detection are:

(1) High contrast. That is, a large difference between the FRET:F ratio in the disassociated state and the FRET:F ratio in the associated state (referred to herein as "delta ratio" ("dR")). In FIG. 2, this is represented as the difference between the highest FRET:F ratio and the lowest FRET:F ratio on the curve.
(2) High sensitivity at physiologically-relevant glucose concentrations when at physiologically-relevant temperatures. In FIG. 2, this is represented by the glucose concentration at the mid-point (which is the steepest part) of the curve. This concentration is referred to herein as "Kd".
(3) Consistency across physiologically-relevant temperatures. That is, the FRET:F ratio at a particular glucose concentration should change as little as possible across temperatures that the molecule may experience.

For such a molecule that is to be used in a subcutaneous implant, the physiologically-relevant temperatures are 32-38 degrees C., e.g., 34-36 degrees C., such as 35 degrees C. It is hypothesized by the inventors that a Kd, at 35 degrees C., of 2-10 mM glucose (e.g., 3-9 mM) is advantageous for such a molecule that is to be used in a subcutaneous implant.

In order to obtain an optimal biosensor, the inventors generated 300 different protein molecules in a bacterial expression system. The molecules included different FRET pairs (donor and acceptor fluorophores), and different links (e.g., linker sequences) between the various portions of the molecules (e.g., between fluorophore amino acid sequences and glucose-binding-region amino acid sequences). The molecules were evaluated for their suitability, e.g., by testing dR, Kd, and for some, consistency across physiologically-relevant temperatures.

As a result of the above experimental approach, the following FRET-based glucose-detection molecules were identified by the inventors as useful FRET-based glucose-detection molecules:

Molecule D274 is defined by SEQ ID No. 1, whose amino acid sequence is as follows:

```
VSELIKENMHMKLYMEGTVNNHHFKCTSEGEGKPYEGTQTMRIKAVEGGPLPFAFDILAT      60
SFMYGSKTFINHTQGIPDFFKQSFPEGFTWERVTTYEDGGVLTATQDTSLQDGCLIYNVK     120
IRGVNFPSNGPVMQKKTLGWEASTETLYPADGGLEGRADMALKLVGGGHLICNLKTTYRS     180
KKPAKNLKMPGVYYVDRRLERIKEADKETYVEQHEVAVARYCDLPSKLGHRADTRIGVTI     240
YKYDDNQMSVVRKAIEQDAKAAPDVQLLMNDSQNDQSKQNDQIDVLLAKGVKALAINLVD     300
PAAAGTVIEKARGQNVPVVFFNKEPSRKALDSYDKAYYVGTDSKESGIIQGDLIAKHWAA     360
NQGWDLNKDGQIQFVLLKGEPGHPDAEARTTYVIKELNDKGIKTEQLQLDTAMWDTAQAK     420
DKMDAWLSGPNANKIEVVIANNDAMAMGAVEALKAHNKSSIPVFGVDALPEALALVKSGA     480
LAGTVLNDANNQAKATFDLAKNLADSKGEELFTGVVPILVELDGDVNGHKFSVRGEGEGD     540
ATNGKLTLKFICTTGKLPVPWPTLVTTFGYGVACFSRYPDHMKQHDFFKSAMPEGYVQER     600
TISFKDDGTYKTRAEVKFEGDTLVNRIELKGIDFKEDGNILGHKLEYNFNSHNVYITADK     660
QKNGIKANFKIRHNVEDGSVQLADHYQQNTPIGDGPVLLPDNHYLSHQSALSKDPNEKRD     720
HMVLLEFVTAAGITHGMDELGAADGTNWKIDNKVVRVPYVGVDKDNLAEFSKK          773
```

Molecule D277 is defined by SEQ ID No. 2, whose amino acid sequence is as follows:

```
VSELIKENMHMKLYMEGTVNNHHFKCTSEGEGKPYEGTQTMRIKAVEGGPLPFAFDILAT      60
SFMYGSKTFINHTQGIPDFFKQSFPEGFTWERVTTYEDGGVLTATQDTSLQDGCLIYNVK     120
IRGVNFPSNGPVMQKKTLGWEASTETLYPADGGLEGRADMALKLVGGGHLICNLKTTYRS     180
KKPAKNLKMPGVYYVDRRLERIKEADKETYVEQHEVAVARYCDLPSKLGHKLNGMDEADT     240
RIGVTIYKYDDNQMSVVRKAIEQDAKAAPDVQLLMNDSQNDQSKQNDQIDVLLAKGVKAL     300
AINLVDPAAAGTVIEKARGQNVPVVFFNKEPSRKALDSYDKAYYVGTDSKESGIIQGDLI     360
AKHWAANQGWDLNKDGQIQFVLLKGEPGHPDAEARTTYVIKELNDKGIKTEQLQLDTAMW     420
```

```
DTAQAKDKMDAWLSGPNANKIEVVIANNDAMAMGAVEALKAHNKSSIPVFGVDALPEALA    480
LVKSGALAGTVLNDANNQAKATFDLAKNLADSKGEELFTGVVPILVELDGDVNGHKFSVR    540
GEGEGDATNGKLTLKFICTTGKLPVPWPTLVTTFGYGVACFSRYPDHMKQHDFFKSAMPE    600
GYVQERTISFKDDGTYKTRAEVKFEGDTLVNRIELKGIDFKEDGNILGHKLEYNFNSHNV    660
YITADKQKNGIKANFKIRHNVEDGSVQLADHYQQNTPIGDGPVLLPDNHYLSHQSALSKD    720
PNEKRDHMVLLEFVTAAGITHGMDELGAADGTNWKIDNKVVRVPYVGVDKDNLAEFSKK     779
```

Molecule D278 is defined by SEQ ID No. 3, whose amino acid sequence is as follows:

```
VSELIKENMHMKLYMEGTVNNHHFKCTSEGEGKPYEGTQTMRIKAVEGGPLPFAFDILAT     60
SFMYGSKTFINHTQGIPDFFKQSFPEGFTWERVTTYEDGGVLTATQDTSLQDGCLIYNVK    120
IRGVNFPSNGPVMQKKTLGWEASTETLYPADGGLEGRADMALKLVGGGHLICNLKTTYRS    180
KKPAKNLKMPGVYYVDRRLERIKEADKETYVEQHEVAVARYCDLPSKLGHKLNGMDEADT    240
RIGVTIYKYDDNQMSVVRKAIEQDAKAAPDVQLLMNDSQNDQSKQNDQIDVLLAKGVKAL    300
AINLVDPAAAGTVIEKARGQNVPVVFFNKEPSRKALDSYDKAYYVGTDSKESGIIQGDLI    360
AKHWAANQGWDLNKDGQIQFVLLKGEPGHPDAEARTTYVIKELNDKGIKTEQLQLDTAMW    420
DTAQAKDKMDAWLSGPNANKIEVVIANNDAMAMGAVEALKAHNKSSIPVFGVDALPEALA    480
LVKSGALAGTVLNDANNQAKATFDLAKNLADSKGEELFTGVVPILVELDGDVNGHKFSVR    540
GEGEGDATNGKLTLKFICTTGKLPVPWPTLVTTFGYGVACFSRYPDHMKQHDFFKSAMPE    600
GYVQERTISFKDDGTYKTRAEVKFEGDTLVNRIELKGIDFKEDGNILGHKLEYNFNSHNV    660
YITADKQKNGIKANFKIRHNVEDGSVQLADHYQQNTPIGDGPVLLPDNHYLSHQSALSKD    720
PNEKRDHMVLLEFVTAAGITHGMDGAADGTNWKIDNKVVRVPYVGVDKDNLAEFSKK      777
```

Molecule D279 is defined by SEQ ID No. 4, whose amino acid sequence is as follows:

```
VSELIKENMHMKLYMEGTVNNHHFKCTSEGEGKPYEGTQTMRIKAVEGGPLPFAFDILAT     60
SFMYGSKTFINHTQGIPDFFKQSFPEGFTWERVTTYEDGGVLTATQDTSLQDGCLIYNVK    120
IRGVNFPSNGPVMQKKTLGWEASTETLYPADGGLEGRADMALKLVGGGHLICNLKTTYRS    180
KKPAKNLKMPGVYYVDRRLERIKEADKETYVEQHEVAVARYCDLPSKLGHRADTRIGVTI    240
YKYDDNQMSVVRKAIEQDAKAAPDVQLLMNDSQNDQSKQNDQIDVLLAKGVKALAINLVD    300
PAAAGTVIEKARGQNVPVVFFNKEPSRKALDSYDKAYYVGTDSKESGIIQGDLIAKHWAA    360
NQGWDLNKDGQIQFVLLKGEPGHPDAEARTTYVIKELNDKGIKTEQLQLDTAMWDTAQAK    420
DKMDAWLSGPNANKIEVVIANNDAMAMGAVEALKAHNKSSIPVFGVDALPEALALVKSGA    480
LAGTVLNDANNQAKATFDLAKNLADGEELFTGVVPILVELDGDVNGHKFSVRGEGEGDAT    540
NGKLTLKFICTTGKLPVPWPTLVTTFGYGVACFSRYPDHMKQHDFFKSAMPEGYVQERTI    600
SFKDDGTYKTRAEVKFEGDTLVNRIELKGIDFKEDGNILGHKLEYNFNSHNVYITADKQK    660
NGIKANFKIRHNVEDGSVQLADHYQQNTPIGDGPVLLPDNHYLSHQSALSKDPNEKRDHM    720
VLLEFVTAAGITHGMDGAADGTNWKIDNKVVRVPYVGVDKDNLAEFSKK              769
```

Molecule D137 is defined by SEQ ID No. 5, whose amino acid sequence is as follows:

```
VSKGEELIKENMHTKLYMEGTVNNHHFKCTHEGEGKPYEGTQTNRIKVVEGGPLPFAFDI    60
LATCFMYGSKTFINHTQGIPDFFKQSFPEGFTWERVTTYEDGGVLTVTQDTSLQDGCLIY   120
NVKLRGVNFPSNGPVMQKKTLGWEASTETLYPADGGLEGRCDMALKLVGGGHLHCNLKTT   180
YRSKKPAKNLKMPGVYFVDRRLERIKEADNETYVEQHEVAVARYCDLPSKLGHKLNGMDE   240
ADTRIGVTIYKYDDNAMSVVRKAIEQDAKAAPDVQLLMNDSQNDQSKQNDQIDVLLAKGV   300
KALAINLVDPAAAGTVIEKARGQNVPVVFFNKEPSRKALDSYDKAYYVGTDSKESGIIQG   360
DLIAKHWAANQGWDLNKDGQIQFVLLKGEPGHPDAEARTTYVIKELNDKGIKTEQLQLDT   420
AMWDTAQAKDKMDAWLSGPNANKIEVVIANNDAMAMGAVEALKAHNKSSIPVFGVDALPE   480
ALALVKSGALAGTVLNDANNQAKATFDLAKNLADMVSKGEELFTGVVPILVELDGDVNGH   540
KFSVRGEGEGDATNGKLTLKFICTTGKLPVPWPTLVTTFGYGVACFSRYPDHMKQHDFFK   600
SAMPEGYVQERTISFKDDGTYKTRAEVKFEGDTLVNRIELKGIDFKEDGNILGHKLEYNF   660
NSHNVYITADKQKNGIKANFKIRHNVEDGSVQLADHYQQNTPIGDGPVLLPDNHYLSHQS   720
ALSKDPNEKRDHMVLLEFVTAAGITHGMDELYKGAADGTNWKIDNKVVRVPYVGVDKDNL   780
AEFSKK                                                         786
```

Molecule D138 is defined by SEQ ID No. 6, whose amino acid sequence is as follows:

```
VSKGEELIKENMHTKLYMEGTVNNHHFKCTHEGEGKPYEGTQTNRIKVVEGGPLPFAFDI    60
LATCFMYGSKTFINHTQGIPDFFKQSFPEGFTWERVTTYEDGGVLTVTQDTSLQDGCLIY   120
NVKLRGVNFPSNGPVMQKKTLGWEASTETLYPADGGLEGRCDMALKLVGGGHLHCNLKTT   180
YRSKKPAKNLKMPGVYFVDRRLERIKEADNETYVEQHEVAVARYCDLPSKLGHKLNGMDE   240
ADTRIGVTIYKYDDNAMSVVRKAIEQDAKAAPDVQLLMNDSQNDQSKQNDQIDVLLAKGV   300
KALAINLVDPAAAGTVIEKARGQNVPVVFFNKEPSRKALDSYDKAYYVGTDSKESGIIQG   360
DLIAKHWAANQGWDLNKDGQIQFVLLKGEPGHPDAEARTTYVIKELNDKGIKTEQLQLDT   420
AMWDTAQAKDKMDAWLSGPNANKIEVVIANNDAMAMGAVEALKAHNKSSIPVFGVDALPE   480
ALALVKSGALAGTVLNDANNQAKATFDLAKNLADMVSKGEELFTGVVPILVELDGDVNGH   540
KFSVRGEGEGDATNGKLTLKFICTTGKLPVPWPTLVTTFGYGVACFSRYPDHMKQHDFFK   600
SAMPEGYVQERTISFKDDGTYKTRAEVKFEGDTLVNRIELKGIDFKEDGNILGHKLEYNF   660
NSHNVYITADKQKNGIKANFKIRHNVEDGSVQLADHYQQNTPIGDGPVLLPDNHYLSHQS   720
ALSKDPNEKRDHMVLLEFVTAAGITHGMDGAADGTNWKIDNKVVRVPYVGVDKDNLAEFS   780
KK                                                             782
```

Figure 3:
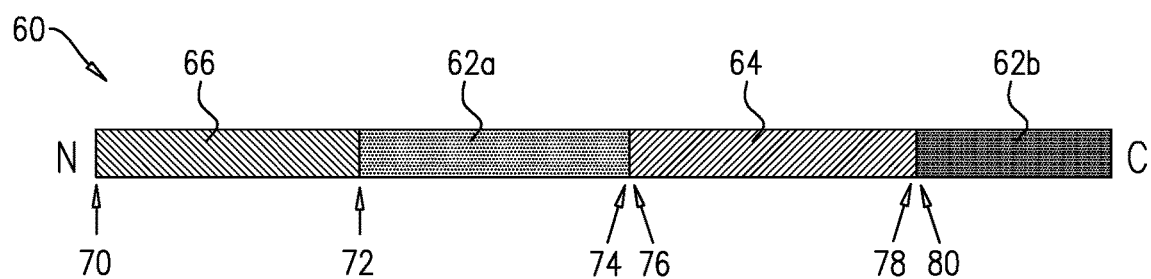
FIG. 3 is a schematic illustration of a generalized amino acid chain of the generalized molecule, in accordance with some applications of the invention.

Reference is now made to FIG. 3, which is a schematic illustration of a generalized amino acid chain 60 of generalized molecule 20, in accordance with some applications of the invention. Amino acid chain 60 is thereby a generalization of the amino acid chains of the FRET-based glucose-detection molecules described hereinabove, in accordance with some applications of the invention. It is to be understood that FIG. 3 is intended to show certain features of the amino acid chain of each of the FRET-based glucose-detection molecules described hereinabove, in order to schematically illustrate commonalities and differences between the FRET-based glucose-detection molecules described herein. In particular, it is to be understood that FIG. 3 is intended to illustrate presence or absence of certain sequences, and/or the order in which certain sequences within the amino acid chains are disposed with respect to each other, and is not intended to represent the relative lengths of those sequences.

An acceptor-fluorophore amino acid sequence 66 defines acceptor fluorophore region 25 (and thereby acceptor fluorophore 26), and is located near (e.g., at) the N-terminus of chain 60. Further along chain 60 is a glucose-binding-region amino acid sequence 62a, which defines glucose-binding site 28. Still further along chain 60 is a donor-fluorophore amino acid sequence 64, which defines donor fluorophore region 23 (and thereby donor fluorophore 24). Still further along chain 60, near (e.g., at) the C-terminus of chain 60 is a second glucose-binding-region amino acid sequence 62b. Glucose-binding region 22 is derived from *E. coli* mg1B (galactose binding protein), whose sequence is modified, inter alia by division into sequences 62a and 62b, with sequence 66 therebetween. Although glucose-binding site 28 is defined by sequence 62a, glucose-binding region 22 as a whole may be considered to be defined by sequences 62a and 62b together. Sequences 66, 62a, 64, and 62b are present in all of the molecules described hereinabove, and in the order shown in FIG. 3.

Generalized amino acid chain 60 also comprises sequences 70, 72, 74, 76, 78, and 80, which are each present in at least one of the molecules described hereinabove, in the order shown with respect to the other sequences that are present in the molecule.

Sequence 70 is present only in molecules D137 and D138, in which the sequence is at the N-terminal end of the molecule. Sequence 70 may also define part of the acceptor fluorophore.

Sequence 72 is present only in molecules D137, D138, D277, and D278, in which the sequence connects sequence 66 to sequence 62a.

Sequence 74 is present only in molecules D137 and D138, in which the sequence connects sequence 62a to the subsequent sequence.

Sequence 76 is present only in molecules D274, D277, D278, D137, and D138, in which the sequence connects the previous sequence (sequence 62a, for D274, D277, and D278; sequence 74 for D137 and D138) to sequence 64.

Sequence 78 is present only in molecules D137, D274, and D277, in which the sequence connects sequence 64 to the subsequent sequence (sequence 62b for D274 and D277; sequence 80 for D137).

Sequence 80 is present only in molecule D137, in which the sequence connects sequence 78 to sequence 62b.

Therefore:
sequence 70 may be described as an N-terminal sequence that is present in a subset of the molecules described hereinabove;
sequence 72 may be described as a linker sequence that links sequences 66 and 62a in a subset of the molecules described hereinabove;
sequences 74 and 76 may be described as linker sequences that link sequences 62a and 64 in subsets of the molecules described hereinabove; and
sequences 78 and 80 may be described as linker sequences that link sequences 64 and 62b in subsets of the molecules described hereinabove.

Sequence 70 has the following amino acid sequence:

VSK                  3

Typically, sequence 66 has SEQ ID No. 7, whose amino acid sequence is:

```
XXELIKENMHXKLYMEGTVNNHHFKCTXEGEGKPYEGTQTXRIKXVEGGPLPFAFDILAT    60

XFMYGSKTFINHTQGIPDFFKQSFPEGFTWERVTTYEDGGVLTXTQDTSLQDGCLIYNVK   120

XRGVNFPSNGPVMQKKTLGWEASTETLYPADGGLEGRXDMALKLVGGGHLXCNLKTTYRS   180

KKPAKNLKMPGVYXVDRRLERIKEADXETYVEQHEVAVARYCDLPSKLGHX           231
```

In SEQ ID No. 7, each X represents a residue that may be one or another amino acid, according to the following:
1—X can be G or V (both of which are aliphatic)
2—X can be E or S
11—X can be T or M
28—X can be H or S
41—X can be N or M
45—X can be V or A (both of which are aliphatic)
61—X can be C or S
104—X can be V or A (both of which are aliphatic)
121—X can be L or I (both of which are aliphatic)
158—X can be C or A
171—X can be H or I
194—X can be F or Y (both of which are aromatic)
207—X can be N or K
231—X can be K or R (both of which are basic)

Sequence 72 has SEQ ID No. 8, whose amino acid sequence is:

```
5          LNGMDE              6
```

As described hereinabove, sequence 72 may be described as a linker sequence that links sequences 66 and 62a, i.e., that links acceptor fluorophore region 25 to glucose-binding region 22 (and thereby to the rest of the molecule) in a manner that facilitates FRET-based glucose detection functionality. It is hypothesized that sequence 72 may also be used in other FRET-based glucose-detection molecules, by linking other acceptor fluorophore regions (i.e., regions that define other fluorophores) to glucose-binding region 22.

Typically, sequence 62a has SEQ ID No. 9, whose amino acid sequence is:

```
ADTRIGVTIYKYDDNXMSVVRKAIEQDAKAAPDVQLLMNDSQNDQSKQNDQIDVLLAKGV      60

KALAINLVDPAAAGTVIEKARGQNVPVVFFNKEPSRKALDSYDKAYYVGTDSKESGIIQG     120

DLIAKHWAANQGWDLNKDGQIQFVLLKGEPGHPDAEARTTYVIKELNDKGIKTEQLQLDT     180

AMWDTAQAKDKMDAWLSGPNANKIEVVIANNDAMAMGAVEALKAHNKSSIPVFGVDALPE     240

ALALVKSGALAGTVLNDANNQAKATFDLAKNLAD                              274
```

In SEQ ID No. 9, residue 16 (represented by an X) may be a hydrophilic, polar (e.g., uncharged polar), and/or amidic amino acid, such as Q (e.g., as for molecules D274, D277, D278, and D279), or N (e.g., as described hereinbelow). For some applications, residue 16 is A (e.g., as for molecules D137 and D138). Alternatively, and as described hereinbelow, residue 16 may be V.

Sequence 74 has the following amino acid sequence:

```
              MV                2
```

Sequence 76 has the following amino acid sequence:

```
              SK                2
```

Sequence 64 has SEQ ID No. 10, whose amino acid sequence is:

```
GEELFTGVVPILVELDGDVNGHKFSVRGEGEGDATNGKLTLKFICTTGKLPVPWPTLVTT      60

FGYGVACFSRYPDHMKQHDFFKSAMPEGYVQERTISFKDDGTYKTRAEVKFEGDTLVNRI     120

ELKGIDFKEDGNILGHKLEYNFNSHNVYITADKQKNGIKANFKIRHNVEDGSVQLADHYQ     180

QNTPIGDGPVLLPDNHYLSHQSALSKDPNEKRDHMVLLEFVTAAGITHGMD             231
```

Sequence 78 has the following amino acid sequence:

```
            EL                            2
```

Sequence 80 has the following amino acid sequence:

```
            YK                            2
```

Sequence 62b has SEQ ID No. 11, whose amino acid sequence is:

```
GAADGTNWKIDNKVVRVPYVGVDKDNLAEFSKK         33
```

There is therefore provided, in accordance with some applications of the invention, a protein having a glucose-binding domain, the protein having an amino acid chain, the amino acid chain comprising, in order: SEQ ID No. 7; SEQ ID No. 9; SEQ ID No. 10; and SEQ ID No. 11. For some such applications:

the amino acid chain further comprises sequence 70 before SEQ ID No. 7;

the amino acid chain further comprises SEQ ID No. 8 between SEQ ID No. 7 and SEQ ID No. 9;

the amino acid chain further comprises sequence 76 between SEQ ID No. 9 and SEQ ID No. 10 (and may further comprise sequence 74 between SEQ ID No. 9 and sequence 76); and/or the amino acid chain further comprises sequence 78 between SEQ ID No. 10 and SEQ ID No. 11 (and may further comprise sequence 80 between sequence 78 and SEQ ID No. 11).

In accordance with some applications of the invention, a protein is provided having a glucose-binding domain, the protein having an amino acid chain, the amino acid chain comprising, in order:

optionally, sequence 70;

SEQ ID No. 7;

optionally, SEQ ID No. 8;

SEQ ID No. 9;

optionally, sequence 74;

optionally, sequence 76;

SEQ ID No. 10;

optionally, sequence 78;

optionally, sequence 80; and

SEQ ID No. 11.

Figure 4:
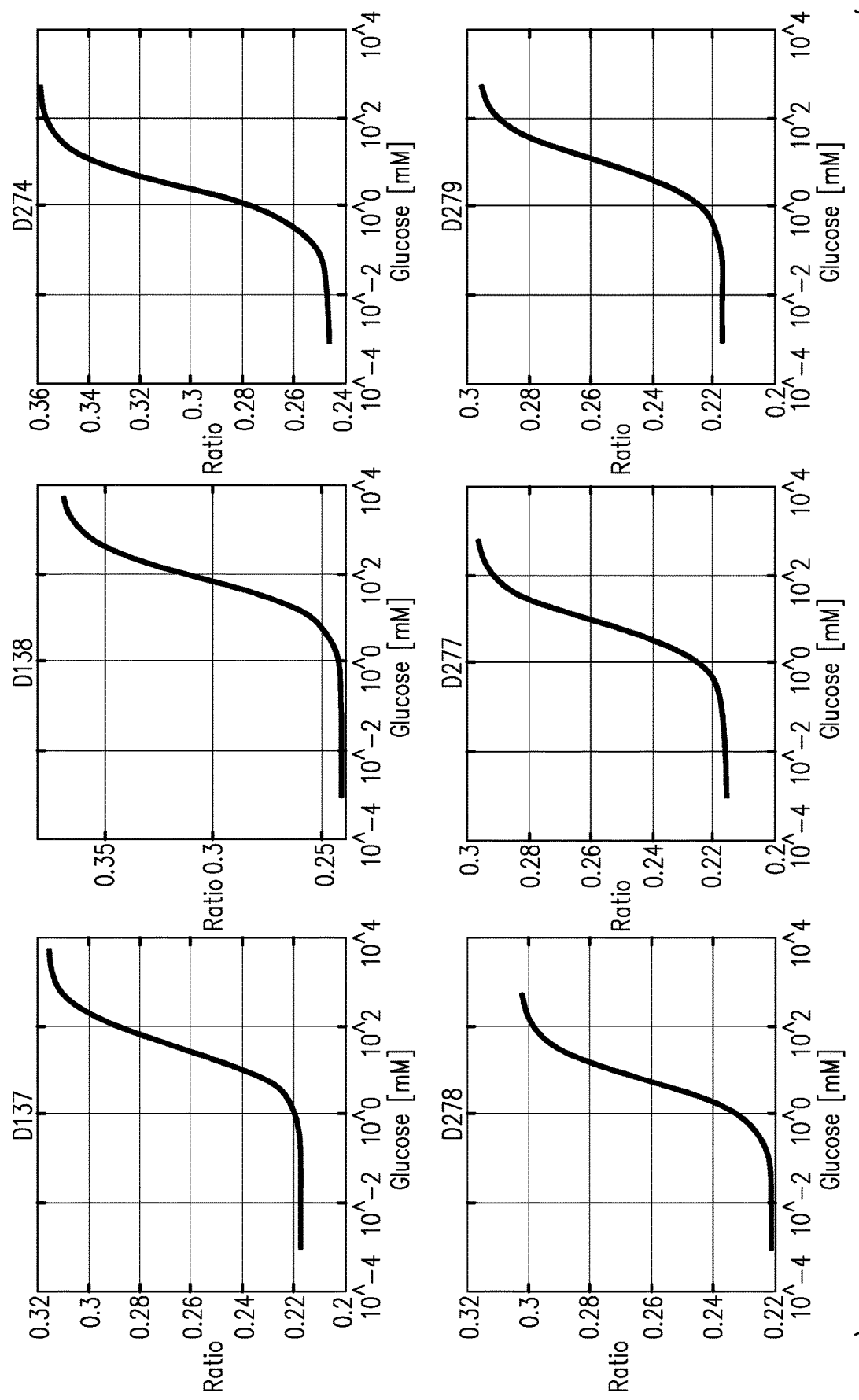
FIG. 4 is a set of graphs which show, for some of the glucose-detecting molecules described, a FRET:F ratio at different glucose concentrations, measured at 35 degrees C., in accordance with some applications of the invention.

Reference is now made to FIG. 4, which is a set of graphs which show, for some of the molecules described hereinabove, the FRET:F ratio (y axis) at different glucose concentrations, measured at 35 degrees C.

The measurements were performed on proteins that were extracted from *E. coli* (in which they were produced) and purified in 50 mM Tris (pH 7.6, 1 mM CaCl_2, 100 mM NaCl_2). Measurements were performed using an Infinite (R) 200 plate reader or on a fluoroscopic microscope. FRET-based emission was measured by applying excitation at 475 nm and detecting emission at 640-800 nm. Direct fluorescence of the acceptor fluorophore was measured by applying excitation at 575 nm and detecting emission at 640-800 nm. Curves were generated from the measured points (typically 10) by a non-linear interpolation, and Kd and dR were extracted.

The data may be summarized as follows:

| | | |
|---|---|---|
| D137: | Kd = 37.8 mM glucose | dR = 46 percent |
| D138: | Kd = 79.7 mM glucose | dR = 54 percent |
| D274: | Kd = 2.7 mM glucose | dR = 47 percent |
| D277: | Kd = 7.2 mM glucose | dR = 38 percent |
| D278: | Kd = 5.8 mM glucose | dR = 37 percent |
| D279: | Kd = 9.9 mM glucose | dR = 37 percent |

As described hereinabove, sequences 62a and 62b are derived from *E. coli* mglB (divided between sequence 62a and sequence 62b). mglB is described, inter alia, in Vyas N K et al. (Science. 1988 Dec. 2; 242(4883):1290-5), and Deuschle K et al. (Protein Sci. 2005 September; 14(9):2304-14), and is archived at The Universal Protein Resource (UniProt; uniprot.org/uniprot/) as P0AEE5. These references are incorporated herein by reference.

In mglB, residues 16 and 183 are key residues of the glucose-binding site. In the FRET-based glucose detection molecules described herein, these residues correspond to residues 16 and 183, respectively, of sequence 62a (e.g., of SEQ ID No. 9). Throughout this patent application, unless stated otherwise, reference to "residue 16" refers to this residue 16 (either the residue 16 of sequence 62a, or the corresponding residue in mglB).

In wild-type mglB, residue 16 is F (Phe/Phenylalanine). In D137 and D138, residue 16 is A (Ala/Alanine), which has been previously described (e.g., Deuschle K et al). In D274, D277, D278, and D279, residue 16 is Q (Gln/Glutamine), which (i) unlike F or A, is hydrophilic, (ii) unlike F or A, is polar (e.g., uncharged polar), and (iii) unlike F or A, is amidic. It is hypothesized by the inventors that the advantageous reduction in Kd between (i) D137 and D138, and (ii) D274, D277, D278, and D279 (which brings the Kd of these molecules into the desirable range described hereinabove) is due to the substitution of the hydrophobic phenylalanine or alanine, with the hydrophilic, polar (e.g., uncharged polar), and amidic glutamine.

There is therefore provided, a glucose-binding molecule comprising an amino acid chain that has a glucose-binding-region amino acid sequence having SEQ ID No. 9, in which residue 16 is glutamine.

Placement of N (Asn/Asparagine) at residue 16 of sequence 62a was also tested. In a similar FRET-based glucose-detection molecule (of which molecule 20 is also representative), the following variants of residue 16 of sequence were performed at room temperature:

| | | |
|---|---|---|
| D198 (16 = A): | Kd = 3.2 mM glucose | dR = 29.1 percent |
| D241 (16 = Q): | Kd = 0.3 mM glucose | dR = 21.4 percent |
| D267 (16 = N): | Kd = 9.4 mM glucose | dR = 32.3 percent |
| D263 (16 = V): | Kd = 7.9 mM glucose | dR = 31.7 percent |

It is to be noted that because these tests were performed at room temperature, the results are not directly comparable with those described with reference to FIGS. 4 and 5, which derive from tests performed at higher temperatures. Nonetheless, at least due to the demonstrated functionality of molecule D267, there is provided a glucose-binding molecule comprising an amino acid chain that has a glucose-binding-region amino acid sequence having SEQ ID No. 9, in which residue 16 is a hydrophilic, polar (e.g., uncharged polar), and/or amidic amino acid.

The results from molecule D263 suggest that for some applications, residue 16 may be valine. Nonetheless, the inventors hypothesize that the presence of a hydrophilic, polar (e.g., uncharged polar), and/or amidic amino acid (e.g., glutamine) at residue 16 of sequence 62a (i.e., of SEQ ID No. 9) makes molecules based on molecule 20 particularly suitable for in vivo FRET-based glucose-detection.

Figure 5A:
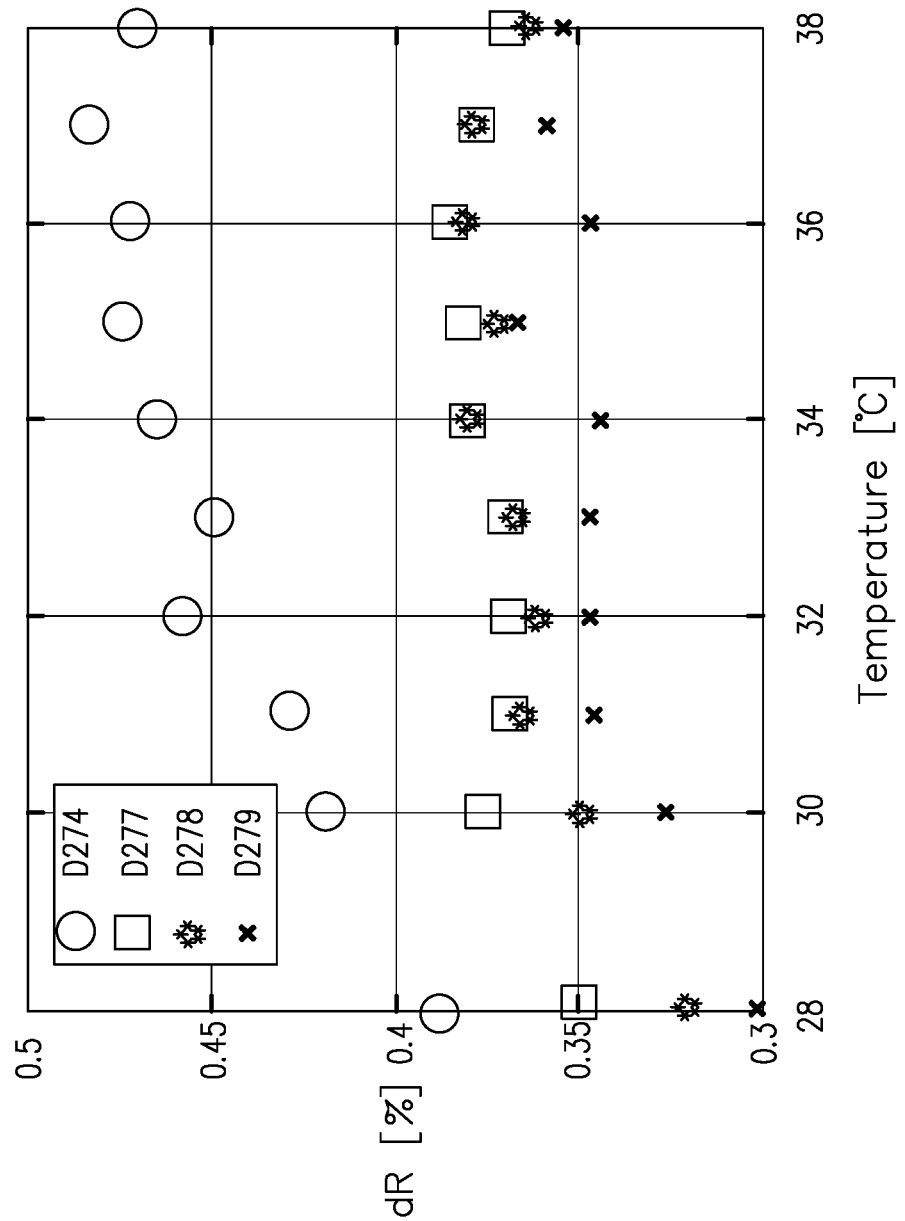
FIGS. 5A-B are graphs showing function of some of the glucose-detecting molecules at different temperatures, in accordance with some applications of the invention.
Figure 5B:
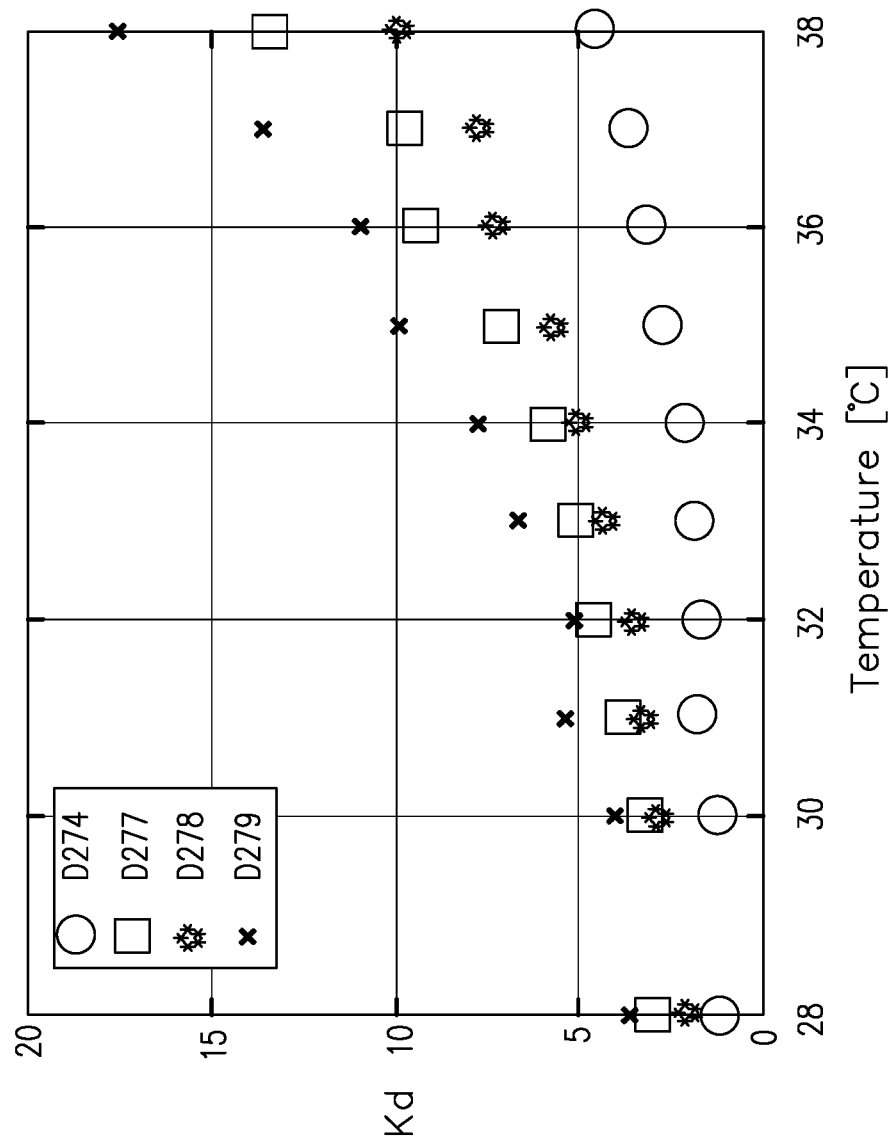

Reference is made to FIGS. 5A-B, which are graphs showing function of some of the glucose-detecting molecules at different temperatures, in accordance with some applications of the invention. dR and Kd were measured for D274, D277, D278 and D279 at different temperatures, as described hereinabove, mutatis mutandis. FIG. 5A shows dR for molecules D274, D277, D278 and D279 at different temperatures, and FIG. 5B shows Kd for the same molecules at the same temperatures. Between 31 and 38 degrees C., the respective dR of molecules D277, D278 and D279 remained somewhat stable, whereas the dR of molecule D274 increased with temperature. Kd increased with temperature for all four molecules; the change was greatest for D279, and smallest for D274.

The understanding of temperature-based changes in Kd and dR for a particular FRET-based glucose detection molecule, and/or the identification of molecules with relatively temperature-stable Kd and/or dR is hypothesized by the inventors to improve the accuracy of FRET-based glucose-detection systems in which such molecules are used.

Reference is again made to FIGS. 1-5B. As described hereinabove, the FRET-based glucose-detection molecules described herein are configured for use in a glucose-detecting implant, e.g., that operates with an extracorporeal (e.g., skin-mounted) detector that detects light emitted from the acceptor fluorophore. It is to be noted that the scope of the invention includes not only the protein sequences described herein, but also (i) gene sequences that encode these protein sequences, (ii) cells (e.g., mammalian cells) containing such gene sequences, and (iii) implants containing these protein sequences or gene sequences, and/or cells containing these protein sequences or gene sequences.

Additionally, the present disclosure contemplates sequences having at least 80%, at least 85%, at least 90%, at least 91%, at least 92%, at least 93%, at least 94%, at least 95%, at least 96%, at least 97%, at least 98%, or at least 99%, sequence identity to a reference sequence, wherein the reference sequence may include, for example, any of SEQ ID NOs: 1, 2, 3, 4, 5, 6, 7, 8, 9, 10, 11, or 12, or any of sequences 70, 66, 72, 62a, 74, 76, 64, 78, 80, or 62b.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A protein having a glucose-binding site, the protein comprising an amino acid chain, the amino acid chain comprising an amino acid sequence greater than 98 percent identical to SEQ ID No. 9, wherein residue 16 of SEQ ID No. 9 is located at the glucose-binding site, and is a hydrophilic amino acid other than Cys.

2. The protein of claim 1, wherein the amino acid sequence is SEQ ID No. 9.

3. The protein of claim 1, wherein amino acid 16 of SEQ ID No. 9 is a polar amino acid.

4. The protein of claim 3, wherein amino acid 16 of SEQ ID No. 9 is an uncharged polar amino acid.

5. The protein of claim 4, wherein amino acid 16 of SEQ ID No. 9 is Gln.

6. The protein of claim 4, wherein amino acid 16 of SEQ ID No. 9 is Asn.

7. The protein of claim 1, wherein amino acid 16 of SEQ ID No. 9 is an amidic amino acid.

8. The protein of claim 7, wherein amino acid 16 of SEQ ID No. 9 is Gln.

9. The protein of claim 7, wherein amino acid 16 of SEQ ID No. 9 is Asn.

10. The protein of claim 1, wherein:
the amino acid sequence is a first amino acid sequence,
the amino acid chain further comprises a second amino acid sequence that is greater than 98 percent identical to SEQ ID No. 11, and
the first amino acid sequence is closer to an N-terminal end of the protein than is the second amino acid sequence.

11. The protein of claim 10, wherein the N-terminal end of the second amino acid sequence begins immediately after the C-terminal end of the first amino acid sequence.

12. The protein of claim 10, wherein the amino acid chain further comprises a fluorophore amino acid sequence that defines a fluorophore and is located between the C-terminal end of the first amino acid sequence and the N-terminal end of the second amino acid sequence.

13. The protein of claim 12, wherein the fluorophore amino acid sequence is a donor-fluorophore amino acid sequence, and defines a donor fluorophore.

14. The protein of claim 13, wherein the amino acid chain further comprises an acceptor-fluorophore amino acid sequence that defines an acceptor fluorophore, wherein:
the first amino acid sequence is between the donor-fluorophore amino acid sequence and the acceptor-fluorophore amino acid sequence, and
the acceptor fluorophore is excitable by the donor fluorophore by Förster Resonance Energy Transfer (FRET).

15. The protein of claim 14, wherein the amino acid chain further comprises a linker sequence that connects the acceptor-fluorophore amino acid sequence to the first sequence, and has SEQ ID No. 8.

16. A protein having a glucose-binding domain, the protein comprising an amino acid chain, the amino acid chain comprising, in order: SEQ ID No. 7; SEQ ID No. 9; SEQ ID No. 10; and SEQ ID No. 11.

17. The protein of claim 16, wherein the amino acid chain further comprises a Val-Ser-Lys sequence before SEQ ID No. 7.

18. The protein of claim 16, wherein the amino acid chain further comprises SEQ ID No. 8 between SEQ ID No. 7 and SEQ ID No. 9.

19. The protein of claim 16, wherein the amino acid chain further comprises a Ser-Lys sequence between SEQ ID No. 9 and SEQ ID No. 10.

20. The protein of claim 19, wherein the amino acid chain further comprises a Met-Val sequence between SEQ ID No. 9 and the Ser-Lys sequence.

21. The protein of claim 16, wherein the amino acid chain further comprises a Glu-Leu sequence between SEQ ID No. 10 and SEQ ID No. 11.

22. The protein of claim 21, wherein the amino acid chain further comprises a Tyr-Lys sequence between the Glu-Leu sequence and SEQ ID No. 11.

* * * * *

SEQUENCE LISTING

```
<160> NUMBER OF SEQ ID NOS: 12

<210> SEQ ID NO 1
<211> LENGTH: 773
<212> TYPE: PRT
<213> ORGANISM: Artificial Sequence
<220> FEATURE:
<223> OTHER INFORMATION: Synthetic FRET-based glucose-detection molecule
      D274

<400> SEQUENCE: 1

Val Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
                20                  25                  30

Lys Pro Tyr Glu Gly Thr Gln Thr Met Arg Ile Lys Ala Val Glu Gly
            35                  40                  45

Gly Pro Leu Pro Phe Ala Phe Asp Ile Leu Ala Thr Ser Phe Met Tyr
        50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
                100                 105                 110

Gly Cys Leu Ile Tyr Asn Val Lys Ile Arg Gly Val Asn Phe Pro Ser
            115                 120                 125

Asn Gly Pro Val Met Gln Lys Lys Thr Leu Gly Trp Glu Ala Ser Thr
        130                 135                 140

Glu Thr Leu Tyr Pro Ala Asp Gly Gly Leu Glu Gly Arg Ala Asp Met
145                 150                 155                 160

Ala Leu Lys Leu Val Gly Gly Gly His Leu Ile Cys Asn Leu Lys Thr
                165                 170                 175
```

```
Thr Tyr Arg Ser Lys Lys Pro Ala Lys Asn Leu Lys Met Pro Gly Val
            180                 185                 190
Tyr Tyr Val Asp Arg Arg Leu Glu Arg Ile Lys Glu Ala Asp Lys Glu
        195                 200                 205
Thr Tyr Val Glu Gln His Glu Val Ala Val Ala Arg Tyr Cys Asp Leu
    210                 215                 220
Pro Ser Lys Leu Gly His Arg Ala Asp Thr Arg Ile Gly Val Thr Ile
225                 230                 235                 240
Tyr Lys Tyr Asp Asp Asn Gln Met Ser Val Val Arg Lys Ala Ile Glu
            245                 250                 255
Gln Asp Ala Lys Ala Ala Pro Asp Val Gln Leu Leu Met Asn Asp Ser
        260                 265                 270
Gln Asn Asp Gln Ser Lys Gln Asn Asp Gln Ile Asp Val Leu Leu Ala
    275                 280                 285
Lys Gly Val Lys Ala Leu Ala Ile Asn Leu Val Asp Pro Ala Ala Ala
290                 295                 300
Gly Thr Val Ile Glu Lys Ala Arg Gly Gln Asn Val Pro Val Val Phe
305                 310                 315                 320
Phe Asn Lys Glu Pro Ser Arg Lys Ala Leu Asp Ser Tyr Asp Lys Ala
            325                 330                 335
Tyr Tyr Val Gly Thr Asp Ser Lys Glu Ser Gly Ile Ile Gln Gly Asp
        340                 345                 350
Leu Ile Ala Lys His Trp Ala Ala Asn Gln Gly Trp Asp Leu Asn Lys
    355                 360                 365
Asp Gly Gln Ile Gln Phe Val Leu Leu Lys Gly Glu Pro Gly His Pro
370                 375                 380
Asp Ala Glu Ala Arg Thr Thr Tyr Val Ile Lys Glu Leu Asn Asp Lys
385                 390                 395                 400
Gly Ile Lys Thr Glu Gln Leu Gln Leu Asp Thr Ala Met Trp Asp Thr
            405                 410                 415
Ala Gln Ala Lys Asp Lys Met Asp Ala Trp Leu Ser Gly Pro Asn Ala
        420                 425                 430
Asn Lys Ile Glu Val Val Ile Ala Asn Asn Asp Ala Met Ala Met Gly
    435                 440                 445
Ala Val Glu Ala Leu Lys Ala His Asn Lys Ser Ser Ile Pro Val Phe
450                 455                 460
Gly Val Asp Ala Leu Pro Glu Ala Leu Ala Leu Val Lys Ser Gly Ala
465                 470                 475                 480
Leu Ala Gly Thr Val Leu Asn Asp Ala Asn Asn Gln Ala Lys Ala Thr
            485                 490                 495
Phe Asp Leu Ala Lys Asn Leu Ala Asp Ser Lys Gly Glu Glu Leu Phe
        500                 505                 510
Thr Gly Val Val Pro Ile Leu Val Glu Leu Asp Gly Asp Val Asn Gly
    515                 520                 525
His Lys Phe Ser Val Arg Gly Glu Gly Glu Gly Asp Ala Thr Asn Gly
530                 535                 540
Lys Leu Thr Leu Lys Phe Ile Cys Thr Thr Gly Lys Leu Pro Val Pro
545                 550                 555                 560
Trp Pro Thr Leu Val Thr Thr Phe Gly Tyr Gly Val Ala Cys Phe Ser
            565                 570                 575
Arg Tyr Pro Asp His Met Lys Gln His Asp Phe Phe Lys Ser Ala Met
        580                 585                 590
Pro Glu Gly Tyr Val Gln Glu Arg Thr Ile Ser Phe Lys Asp Asp Gly
```

-continued

```
                595                 600                 605
Thr Tyr Lys Thr Arg Ala Glu Val Lys Phe Glu Gly Asp Thr Leu Val
        610                 615                 620
Asn Arg Ile Glu Leu Lys Gly Ile Asp Phe Lys Glu Asp Gly Asn Ile
625                 630                 635                 640
Leu Gly His Lys Leu Glu Tyr Asn Phe Asn Ser His Asn Val Tyr Ile
            645                 650                 655
Thr Ala Asp Lys Gln Lys Asn Gly Ile Lys Ala Asn Phe Lys Ile Arg
        660                 665                 670
His Asn Val Glu Asp Gly Ser Val Gln Leu Ala Asp His Tyr Gln Gln
            675                 680                 685
Asn Thr Pro Ile Gly Asp Gly Pro Val Leu Leu Pro Asp Asn His Tyr
        690                 695                 700
Leu Ser His Gln Ser Ala Leu Ser Lys Asp Pro Asn Glu Lys Arg Asp
705                 710                 715                 720
His Met Val Leu Leu Glu Phe Val Thr Ala Ala Gly Ile Thr His Gly
            725                 730                 735
Met Asp Glu Leu Gly Ala Ala Asp Gly Thr Asn Trp Lys Ile Asp Asn
        740                 745                 750
Lys Val Val Arg Val Pro Tyr Val Gly Val Asp Lys Asp Asn Leu Ala
            755                 760                 765
Glu Phe Ser Lys Lys
        770

<210> SEQ ID NO 2
<211> LENGTH: 779
<212> TYPE: PRT
<213> ORGANISM: Artificial Sequence
<220> FEATURE:
<223> OTHER INFORMATION: Synthetic FRET-based glucose-detection molecule
      D277

<400> SEQUENCE: 2

Val Ser Glu Leu Ile Lys Glu Asn Met His Met Lys Leu Tyr Met Glu
1               5                   10                  15
Gly Thr Val Asn Asn His His Phe Lys Cys Thr Ser Glu Gly Glu Gly
                20                  25                  30
Lys Pro Tyr Glu Gly Thr Gln Thr Met Arg Ile Lys Ala Val Glu Gly
            35                  40                  45
Gly Pro Leu Pro Phe Ala Phe Asp Ile Leu Ala Thr Ser Phe Met Tyr
        50                  55                  60
Gly Ser Lys Thr Phe Ile Asn His Thr Gln Gly Ile Pro Asp Phe Phe
65                  70                  75                  80
Lys Gln Ser Phe Pro Glu Gly Phe Thr Trp Glu Arg Val Thr Thr Tyr
                85                  90                  95
Glu Asp Gly Gly Val Leu Thr Ala Thr Gln Asp Thr Ser Leu Gln Asp
            100                 105                 110
Gly Cys Leu Ile Tyr Asn Val Lys Ile Arg Gly Val Asn Phe Pro Ser
        115                 120                 125
Asn Gly Pro Val Met Gln Lys Lys Thr Leu Gly Trp Glu Ala Ser Thr
130                 135                 140
Glu Thr Leu Tyr Pro Ala Asp Gly Gly Leu Glu Gly Arg Ala Asp Met
145                 150                 155                 160
Ala Leu Lys Leu Val Gly Gly Gly His Leu Ile Cys Asn Leu Lys Thr
                165                 170                 175
```

```
Thr Tyr Arg Ser Lys Lys Pro Ala Lys Asn Leu Lys Met Pro Gly Val
            180                 185                 190

Tyr Tyr Val Asp Arg Arg Leu Glu Arg Ile Lys Glu Ala Asp Lys Glu
        195                 200                 205

Thr Tyr Val Glu Gln His Glu Val Ala Val Ala Arg Tyr Cys Asp Leu
    210                 215                 220

Pro Ser Lys Leu Gly His Lys Leu Asn Gly Met Asp Glu Ala Asp Thr
225                 230                 235                 240

Arg Ile Gly Val Thr Ile Tyr Lys Tyr Asp Asp Asn Gln Met Ser Val
                245                 250                 255

Val Arg Lys Ala Ile Glu Gln Asp Ala Lys Ala Ala Pro Asp Val Gln
            260                 265                 270

Leu Leu Met Asn Asp Ser Gln Asn Asp Gln Ser Lys Gln Asn Asp Gln
        275                 280                 285

Ile Asp Val Leu Leu Ala Lys Gly Val Lys Ala Leu Ala Ile Asn Leu
    290                 295                 300

Val Asp Pro Ala Ala Ala Gly Thr Val Ile Glu Lys Ala Arg Gly Gln
305                 310                 315                 320

Asn Val Pro Val Val Phe Phe Asn Lys Glu Pro Ser Arg Lys Ala Leu
                325                 330                 335

Asp Ser Tyr Asp Lys Ala Tyr Tyr Val Gly Thr Asp Ser Lys Glu Ser
            340                 345                 350

Gly Ile Ile Gln Gly Asp Leu Ile Ala Lys His Trp Ala Ala Asn Gln
        355                 360                 365

Gly Trp Asp Leu Asn Lys Asp Gly Gln Ile Gln Phe Val Leu Leu Lys
    370                 375                 380

Gly Glu Pro Gly His Pro Asp Ala Glu Ala Arg Thr Thr Tyr Val Ile
385                 390                 395                 400

Lys Glu Leu Asn Asp Lys Gly Ile Lys Thr Glu Gln Leu Gln Leu Asp
                405                 410                 415

Thr Ala Met Trp Asp Thr Ala Gln Ala Lys Asp Lys Met Asp Ala Trp
            420                 425                 430

Leu Ser Gly Pro Asn Ala Asn Lys Ile Glu Val Val Ile Ala Asn Asn
        435                 440                 445

Asp Ala Met Ala Met Gly Ala Val Glu Ala Leu Lys Ala His Asn Lys
    450                 455                 460

Ser Ser Ile Pro Val Phe Gly Val Asp Ala Leu Pro Glu Ala Leu Ala
465                 470                 475                 480

Leu Val Lys Ser Gly Ala Leu Ala Gly Thr Val Leu Asn Asp Ala Asn
                485                 490                 495

Asn Gln Ala Lys Ala Thr Phe Asp Leu Ala Lys Asn Leu Ala Asp Ser
            500                 505                 510

Lys Gly Glu Glu Leu Phe Thr Gly Val Val Pro Ile Leu Val Glu Leu
        515                 520                 525

Asp Gly Asp Val Asn Gly His Lys Phe Ser Val Arg Gly Glu Gly Glu
    530                 535                 540

Gly Asp Ala Thr Asn Gly Lys Leu Thr Leu Lys Phe Ile Cys Thr Thr
545                 550                 555                 560

Gly Lys Leu Pro Val Pro Trp Pro Thr Leu Val Thr Thr Phe Gly Tyr
                565                 570                 575

Gly Val Ala Cys Phe Ser Arg Tyr Pro Asp His Met Lys Gln His Asp
            580                 585                 590

Phe Phe Lys Ser Ala Met Pro Glu Gly Tyr Val Gln Glu Arg Thr Ile
```

```
                        595                 600                 605
Ser Phe Lys Asp Asp Gly Thr Tyr Lys Thr Arg Ala Glu Val Lys Phe
    610                 615                 620

Glu Gly Asp Thr Leu Val Asn Arg Ile Glu Leu Lys Gly Ile Asp Phe
625                 630                 635                 640

Lys Glu Asp Gly Asn Ile Leu Gly His Lys Leu Glu Tyr Asn Phe Asn
                645                 650                 655

Ser His Asn Val Tyr Ile Thr Ala Asp Lys Gln Lys Asn Gly Ile Lys
            660                 665                 670

Ala Asn Phe Lys Ile Arg His Asn Val Glu Asp Gly Ser Val Gln Leu
        675                 680                 685

Ala Asp His Tyr Gln Gln Asn Thr Pro Ile Gly Asp Gly Pro Val Leu
    690                 695                 700

Leu Pro Asp Asn His Tyr Leu Ser His Gln Ser Ala Leu Ser Lys Asp
705                 710                 715                 720

Pro Asn Glu Lys Arg Asp His Met Val Leu Leu Glu Phe Val Thr Ala
                725                 730                 735

Ala Gly Ile Thr His Gly Met Asp Glu Leu Gly Ala Ala Asp Gly Thr
            740                 745                 750

Asn Trp Lys Ile Asp Asn Lys Val Val Arg Val Pro Tyr Val Gly Val
        755                 760                 765

Asp Lys Asp Asn Leu Ala Glu Phe Ser Lys Lys
    770                 775

<210> SEQ ID NO 3
<211> LENGTH: 777
<212> TYPE: PRT
<213> ORGANISM: Artificial Sequence
<220> FEATURE:
<223> OTHER INFORMATION: Synthetic FRET-based glucose-detection molecule
      D278

<400> SEQUENCE: 3

Val Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
                20                  25                  30

Lys Pro Tyr Glu Gly Thr Gln Thr Met Arg Ile Lys Ala Val Glu Gly
            35                  40                  45

Gly Pro Leu Pro Phe Ala Phe Asp Ile Leu Ala Thr Ser Phe Met Tyr
        50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Pro Ser
        115                 120                 125

Asn Gly Pro Val Met Gln Lys Lys Thr Leu Gly Trp Glu Ala Ser Thr
    130                 135                 140

Glu Thr Leu Tyr Pro Ala Asp Gly Gly Leu Glu Gly Arg Ala Asp Met
145                 150                 155                 160

Ala Leu Lys Leu Val Gly Gly Gly His Leu Ile Cys Asn Leu Lys Thr
                165                 170                 175
```

-continued

```
Thr Tyr Arg Ser Lys Lys Pro Ala Lys Asn Leu Lys Met Pro Gly Val
            180                 185                 190
Tyr Tyr Val Asp Arg Arg Leu Glu Arg Ile Lys Glu Ala Asp Lys Glu
        195                 200                 205
Thr Tyr Val Glu Gln His Glu Val Ala Val Ala Arg Tyr Cys Asp Leu
    210                 215                 220
Pro Ser Lys Leu Gly His Lys Leu Asn Gly Met Asp Glu Ala Asp Thr
225                 230                 235                 240
Arg Ile Gly Val Thr Ile Tyr Lys Tyr Asp Asp Asn Gln Met Ser Val
                245                 250                 255
Val Arg Lys Ala Ile Glu Gln Asp Ala Lys Ala Ala Pro Asp Val Gln
            260                 265                 270
Leu Leu Met Asn Asp Ser Gln Asn Asp Gln Ser Lys Gln Asn Asp Gln
        275                 280                 285
Ile Asp Val Leu Leu Ala Lys Gly Val Lys Ala Leu Ala Ile Asn Leu
    290                 295                 300
Val Asp Pro Ala Ala Ala Gly Thr Val Ile Glu Lys Ala Arg Gly Gln
305                 310                 315                 320
Asn Val Pro Val Val Phe Phe Asn Lys Glu Pro Ser Arg Lys Ala Leu
                325                 330                 335
Asp Ser Tyr Asp Lys Ala Tyr Tyr Val Gly Thr Asp Ser Lys Glu Ser
            340                 345                 350
Gly Ile Ile Gln Gly Asp Leu Ile Ala Lys His Trp Ala Ala Asn Gln
        355                 360                 365
Gly Trp Asp Leu Asn Lys Asp Gly Gln Ile Gln Phe Val Leu Leu Lys
    370                 375                 380
Gly Glu Pro Gly His Pro Asp Ala Glu Ala Arg Thr Thr Tyr Val Ile
385                 390                 395                 400
Lys Glu Leu Asn Asp Lys Gly Ile Lys Thr Glu Gln Leu Gln Leu Asp
                405                 410                 415
Thr Ala Met Trp Asp Thr Ala Gln Ala Lys Asp Lys Met Asp Ala Trp
            420                 425                 430
Leu Ser Gly Pro Asn Ala Asn Lys Ile Glu Val Val Ile Ala Asn Asn
        435                 440                 445
Asp Ala Met Ala Met Gly Ala Val Glu Ala Leu Lys Ala His Asn Lys
    450                 455                 460
Ser Ser Ile Pro Val Phe Gly Val Asp Ala Leu Pro Glu Ala Leu Ala
465                 470                 475                 480
Leu Val Lys Ser Gly Ala Leu Ala Gly Thr Val Leu Asn Asp Ala Asn
                485                 490                 495
Asn Gln Ala Lys Ala Thr Phe Asp Leu Ala Lys Asn Leu Ala Asp Ser
            500                 505                 510
Lys Gly Glu Glu Leu Phe Thr Gly Val Val Pro Ile Leu Val Glu Leu
        515                 520                 525
Asp Gly Asp Val Asn Gly His Lys Phe Ser Val Arg Gly Glu Gly Glu
    530                 535                 540
Gly Asp Ala Thr Asn Gly Lys Leu Thr Leu Lys Phe Ile Cys Thr Thr
545                 550                 555                 560
Gly Lys Leu Pro Val Pro Trp Pro Thr Leu Val Thr Thr Phe Gly Tyr
                565                 570                 575
Gly Val Ala Cys Phe Ser Arg Tyr Pro Asp His Met Lys Gln His Asp
            580                 585                 590
Phe Phe Lys Ser Ala Met Pro Glu Gly Tyr Val Gln Glu Arg Thr Ile
```

```
                595                 600                 605
Ser Phe Lys Asp Asp Gly Thr Tyr Lys Thr Arg Ala Glu Val Lys Phe
    610                 615                 620

Glu Gly Asp Thr Leu Val Asn Arg Ile Glu Leu Lys Gly Ile Asp Phe
625                 630                 635                 640

Lys Glu Asp Gly Asn Ile Leu Gly His Lys Leu Glu Tyr Asn Phe Asn
                645                 650                 655

Ser His Asn Val Tyr Ile Thr Ala Asp Lys Gln Lys Asn Gly Ile Lys
            660                 665                 670

Ala Asn Phe Lys Ile Arg His Asn Val Glu Asp Gly Ser Val Gln Leu
        675                 680                 685

Ala Asp His Tyr Gln Gln Asn Thr Pro Ile Gly Asp Gly Pro Val Leu
    690                 695                 700

Leu Pro Asp Asn His Tyr Leu Ser His Gln Ser Ala Leu Ser Lys Asp
705                 710                 715                 720

Pro Asn Glu Lys Arg Asp His Met Val Leu Leu Glu Phe Val Thr Ala
                725                 730                 735

Ala Gly Ile Thr His Gly Met Asp Gly Ala Ala Asp Gly Thr Asn Trp
            740                 745                 750

Lys Ile Asp Asn Lys Val Val Arg Val Pro Tyr Val Gly Val Asp Lys
        755                 760                 765

Asp Asn Leu Ala Glu Phe Ser Lys Lys
    770                 775

<210> SEQ ID NO 4
<211> LENGTH: 769
<212> TYPE: PRT
<213> ORGANISM: Artificial Sequence
<220> FEATURE:
<223> OTHER INFORMATION: Synthetic FRET-based glucose-detection molecule
      D279

<400> SEQUENCE: 4

Val Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Glu Gly Thr Gln Thr Met Arg Ile Lys Ala Val Glu Gly
        35                  40                  45

Gly Pro Leu Pro Phe Ala Phe Asp Ile Leu Ala Thr Ser Phe Met Tyr
    50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Pro Ser
        115                 120                 125

Asn Gly Pro Val Met Gln Lys Lys Thr Leu Gly Trp Glu Ala Ser Thr
    130                 135                 140

Glu Thr Leu Tyr Pro Ala Asp Gly Gly Leu Glu Gly Arg Ala Asp Met
145                 150                 155                 160

Ala Leu Lys Leu Val Gly Gly Gly His Leu Ile Cys Asn Leu Lys Thr
                165                 170                 175
```

-continued

```
Thr Tyr Arg Ser Lys Lys Pro Ala Lys Asn Leu Lys Met Pro Gly Val
            180                 185                 190
Tyr Tyr Val Asp Arg Arg Leu Glu Arg Ile Lys Glu Ala Asp Lys Glu
        195                 200                 205
Thr Tyr Val Glu Gln His Glu Val Ala Val Ala Arg Tyr Cys Asp Leu
        210                 215                 220
Pro Ser Lys Leu Gly His Arg Ala Asp Thr Arg Ile Gly Val Thr Ile
225                 230                 235                 240
Tyr Lys Tyr Asp Asp Asn Gln Met Ser Val Arg Lys Ala Ile Glu
                245                 250                 255
Gln Asp Ala Lys Ala Ala Pro Asp Val Gln Leu Leu Met Asn Asp Ser
                260                 265                 270
Gln Asn Asp Gln Ser Lys Gln Asn Asp Gln Ile Asp Val Leu Leu Ala
            275                 280                 285
Lys Gly Val Lys Ala Leu Ala Ile Asn Leu Val Asp Pro Ala Ala Ala
        290                 295                 300
Gly Thr Val Ile Glu Lys Ala Arg Gly Gln Asn Val Pro Val Val Phe
305                 310                 315                 320
Phe Asn Lys Glu Pro Ser Arg Lys Ala Leu Asp Ser Tyr Asp Lys Ala
                325                 330                 335
Tyr Tyr Val Gly Thr Asp Ser Lys Glu Ser Gly Ile Ile Gln Gly Asp
                340                 345                 350
Leu Ile Ala Lys His Trp Ala Ala Asn Gln Gly Trp Asp Leu Asn Lys
            355                 360                 365
Asp Gly Gln Ile Gln Phe Val Leu Leu Lys Gly Glu Pro Gly His Pro
        370                 375                 380
Asp Ala Glu Ala Arg Thr Thr Tyr Val Ile Lys Glu Leu Asn Asp Lys
385                 390                 395                 400
Gly Ile Lys Thr Glu Gln Leu Gln Leu Asp Thr Ala Met Trp Asp Thr
                405                 410                 415
Ala Gln Ala Lys Asp Lys Met Asp Ala Trp Leu Ser Gly Pro Asn Ala
            420                 425                 430
Asn Lys Ile Glu Val Val Ile Ala Asn Asn Asp Ala Met Ala Met Gly
        435                 440                 445
Ala Val Glu Ala Leu Lys Ala His Asn Lys Ser Ser Ile Pro Val Phe
450                 455                 460
Gly Val Asp Ala Leu Pro Glu Ala Leu Ala Leu Val Lys Ser Gly Ala
465                 470                 475                 480
Leu Ala Gly Thr Val Leu Asn Asp Ala Asn Asn Gln Ala Lys Ala Thr
                485                 490                 495
Phe Asp Leu Ala Lys Asn Leu Ala Asp Gly Glu Glu Leu Phe Thr Gly
            500                 505                 510
Val Val Pro Ile Leu Val Glu Leu Asp Gly Asp Val Asn Gly His Lys
        515                 520                 525
Phe Ser Val Arg Gly Glu Gly Glu Gly Asp Ala Thr Asn Gly Lys Leu
        530                 535                 540
Thr Leu Lys Phe Ile Cys Thr Thr Gly Lys Leu Pro Val Pro Trp Pro
545                 550                 555                 560
Thr Leu Val Thr Thr Phe Gly Tyr Gly Val Ala Cys Phe Ser Arg Tyr
                565                 570                 575
Pro Asp His Met Lys Gln His Asp Phe Phe Lys Ser Ala Met Pro Glu
            580                 585                 590
Gly Tyr Val Gln Glu Arg Thr Ile Ser Phe Lys Asp Asp Gly Thr Tyr
```

```
                595                 600                 605
Lys Thr Arg Ala Glu Val Lys Phe Glu Gly Asp Thr Leu Val Asn Arg
    610                 615                 620

Ile Glu Leu Lys Gly Ile Asp Phe Lys Glu Asp Gly Asn Ile Leu Gly
625                 630                 635                 640

His Lys Leu Glu Tyr Asn Phe Asn Ser His Asn Val Tyr Ile Thr Ala
                645                 650                 655

Asp Lys Gln Lys Asn Gly Ile Lys Ala Asn Phe Lys Ile Arg His Asn
            660                 665                 670

Val Glu Asp Gly Ser Val Gln Leu Ala Asp His Tyr Gln Gln Asn Thr
        675                 680                 685

Pro Ile Gly Asp Gly Pro Val Leu Leu Pro Asp Asn His Tyr Leu Ser
    690                 695                 700

His Gln Ser Ala Leu Ser Lys Asp Pro Asn Glu Lys Arg Asp His Met
705                 710                 715                 720

Val Leu Leu Glu Phe Val Thr Ala Ala Gly Ile Thr His Gly Met Asp
                725                 730                 735

Gly Ala Ala Asp Gly Thr Asn Trp Lys Ile Asp Asn Lys Val Val Arg
            740                 745                 750

Val Pro Tyr Val Gly Val Asp Lys Asp Asn Leu Ala Glu Phe Ser Lys
        755                 760                 765

Lys

<210> SEQ ID NO 5
<211> LENGTH: 786
<212> TYPE: PRT
<213> ORGANISM: Artificial Sequence
<220> FEATURE:
<223> OTHER INFORMATION: Synthetic FRET-based glucose-detection molecule
      D137

<400> SEQUENCE: 5

Val Ser Lys Gly Glu Glu Leu Ile Lys Glu Asn Met His Thr Lys Leu
1               5                   10                  15

Tyr Met Glu Gly Thr Val Asn Asn His His Phe Lys Cys Thr His Glu
            20                  25                  30

Gly Glu Gly Lys Pro Tyr Glu Gly Thr Gln Thr Asn Arg Ile Lys Val
        35                  40                  45

Val Glu Gly Gly Pro Leu Pro Phe Ala Phe Asp Ile Leu Ala Thr Cys
    50                  55                  60

Phe Met Tyr Gly Ser Lys Thr Phe Ile Asn His Thr Gln Gly Ile Pro
65                  70                  75                  80

Asp Phe Phe Lys Gln Ser Phe Pro Glu Gly Phe Thr Trp Glu Arg Val
                85                  90                  95

Thr Thr Tyr Glu Asp Gly Gly Val Leu Thr Val Thr Gln Asp Thr Ser
            100                 105                 110

Leu Gln Asp Gly Cys Leu Ile Tyr Asn Val Lys Leu Arg Gly Val Asn
        115                 120                 125

Phe Pro Ser Asn Gly Pro Val Met Gln Lys Lys Thr Leu Gly Trp Glu
    130                 135                 140

Ala Ser Thr Glu Thr Leu Tyr Pro Ala Asp Gly Gly Leu Glu Gly Arg
145                 150                 155                 160

Cys Asp Met Ala Leu Lys Leu Val Gly Gly Gly His Leu His Cys Asn
                165                 170                 175

Leu Lys Thr Thr Tyr Arg Ser Lys Lys Pro Ala Lys Asn Leu Lys Met
```

```
                180             185                 190
Pro Gly Val Tyr Phe Val Asp Arg Arg Leu Glu Arg Ile Lys Glu Ala
            195                 200                 205

Asp Asn Glu Thr Tyr Val Glu Gln His Glu Val Ala Val Ala Arg Tyr
    210                 215                 220

Cys Asp Leu Pro Ser Lys Leu Gly His Lys Leu Asn Gly Met Asp Glu
225                 230                 235                 240

Ala Asp Thr Arg Ile Gly Val Thr Ile Tyr Lys Tyr Asp Asn Ala
                245                 250                 255

Met Ser Val Val Arg Lys Ala Ile Glu Gln Asp Ala Lys Ala Ala Pro
            260                 265                 270

Asp Val Gln Leu Leu Met Asn Asp Ser Gln Asn Asp Gln Ser Lys Gln
    275                 280                 285

Asn Asp Gln Ile Asp Val Leu Leu Ala Lys Gly Val Lys Ala Leu Ala
    290                 295                 300

Ile Asn Leu Val Asp Pro Ala Ala Ala Gly Thr Val Ile Glu Lys Ala
305                 310                 315                 320

Arg Gly Gln Asn Val Pro Val Val Phe Phe Asn Lys Glu Pro Ser Arg
                325                 330                 335

Lys Ala Leu Asp Ser Tyr Asp Lys Ala Tyr Tyr Val Gly Thr Asp Ser
                340                 345                 350

Lys Glu Ser Gly Ile Ile Gln Gly Asp Leu Ile Ala Lys His Trp Ala
            355                 360                 365

Ala Asn Gln Gly Trp Asp Leu Asn Lys Asp Gly Gln Ile Gln Phe Val
    370                 375                 380

Leu Leu Lys Gly Glu Pro Gly His Pro Asp Ala Glu Ala Arg Thr Thr
385                 390                 395                 400

Tyr Val Ile Lys Glu Leu Asn Asp Lys Gly Ile Lys Thr Glu Gln Leu
                405                 410                 415

Gln Leu Asp Thr Ala Met Trp Asp Thr Ala Gln Ala Lys Asp Lys Met
            420                 425                 430

Asp Ala Trp Leu Ser Gly Pro Asn Ala Asn Lys Ile Glu Val Val Ile
    435                 440                 445

Ala Asn Asn Asp Ala Met Ala Met Gly Ala Val Glu Ala Leu Lys Ala
    450                 455                 460

His Asn Lys Ser Ser Ile Pro Val Phe Gly Val Asp Ala Leu Pro Glu
465                 470                 475                 480

Ala Leu Ala Leu Val Lys Ser Gly Ala Leu Ala Gly Thr Val Leu Asn
                485                 490                 495

Asp Ala Asn Asn Gln Ala Lys Ala Thr Phe Asp Leu Ala Lys Asn Leu
            500                 505                 510

Ala Asp Met Val Ser Lys Gly Glu Glu Leu Phe Thr Gly Val Val Pro
    515                 520                 525

Ile Leu Val Glu Leu Asp Gly Asp Val Asn Gly His Lys Phe Ser Val
    530                 535                 540

Arg Gly Glu Gly Glu Gly Asp Ala Thr Asn Gly Lys Leu Thr Leu Lys
545                 550                 555                 560

Phe Ile Cys Thr Thr Gly Lys Leu Pro Val Pro Trp Pro Thr Leu Val
                565                 570                 575

Thr Thr Phe Gly Tyr Gly Val Ala Cys Phe Ser Arg Tyr Pro Asp His
                580                 585                 590

Met Lys Gln His Asp Phe Phe Lys Ser Ala Met Pro Glu Gly Tyr Val
            595                 600                 605
```

```
Gln Glu Arg Thr Ile Ser Phe Lys Asp Asp Gly Thr Tyr Lys Thr Arg
            610                 615                 620

Ala Glu Val Lys Phe Glu Gly Asp Thr Leu Val Asn Arg Ile Glu Leu
625                 630                 635                 640

Lys Gly Ile Asp Phe Lys Glu Asp Gly Asn Ile Leu Gly His Lys Leu
                645                 650                 655

Glu Tyr Asn Phe Asn Ser His Asn Val Tyr Ile Thr Ala Asp Lys Gln
            660                 665                 670

Lys Asn Gly Ile Lys Ala Asn Phe Lys Ile Arg His Asn Val Glu Asp
        675                 680                 685

Gly Ser Val Gln Leu Ala Asp His Tyr Gln Gln Asn Thr Pro Ile Gly
    690                 695                 700

Asp Gly Pro Val Leu Leu Pro Asp Asn His Tyr Leu Ser His Gln Ser
705                 710                 715                 720

Ala Leu Ser Lys Asp Pro Asn Glu Lys Arg Asp His Met Val Leu Leu
                725                 730                 735

Glu Phe Val Thr Ala Ala Gly Ile Thr His Gly Met Asp Glu Leu Tyr
            740                 745                 750

Lys Gly Ala Ala Asp Gly Thr Asn Trp Lys Ile Asp Asn Lys Val Val
        755                 760                 765

Arg Val Pro Tyr Val Gly Val Asp Lys Asp Asn Leu Ala Glu Phe Ser
770                 775                 780

Lys Lys
785

<210> SEQ ID NO 6
<211> LENGTH: 782
<212> TYPE: PRT
<213> ORGANISM: Artificial Sequence
<220> FEATURE:
<223> OTHER INFORMATION: Synthetic FRET-based glucose-detection molecule
      D138

<400> SEQUENCE: 6

Val Ser Lys Gly Glu Glu Leu Ile Lys Glu Asn Met His Thr Lys Leu
1               5                   10                  15

Tyr Met Glu Gly Thr Val Asn Asn His His Phe Lys Cys Thr His Glu
            20                  25                  30

Gly Glu Gly Lys Pro Tyr Glu Gly Thr Gln Thr Asn Arg Ile Lys Val
        35                  40                  45

Val Glu Gly Gly Pro Leu Pro Phe Ala Phe Asp Ile Leu Ala Thr Cys
    50                  55                  60

Phe Met Tyr Gly Ser Lys Thr Phe Ile Asn His Thr Gln Gly Ile Pro
65                  70                  75                  80

Asp Phe Phe Lys Gln Ser Phe Pro Glu Gly Phe Thr Trp Glu Arg Val
                85                  90                  95

Thr Thr Tyr Glu Asp Gly Gly Val Leu Thr Val Thr Gln Asp Thr Ser
            100                 105                 110

Leu Gln Asp Gly Cys Leu Ile Tyr Asn Val Lys Leu Arg Gly Val Asn
        115                 120                 125

Phe Pro Ser Asn Gly Pro Val Met Gln Lys Lys Thr Leu Gly Trp Glu
    130                 135                 140

Ala Ser Thr Glu Thr Leu Tyr Pro Ala Asp Gly Gly Leu Glu Gly Arg
145                 150                 155                 160

Cys Asp Met Ala Leu Lys Leu Val Gly Gly Gly His Leu His Cys Asn
```

```
            165                 170                 175
Leu Lys Thr Thr Tyr Arg Ser Lys Lys Pro Ala Lys Asn Leu Lys Met
            180                 185                 190
Pro Gly Val Tyr Phe Val Asp Arg Arg Leu Glu Arg Ile Lys Glu Ala
            195                 200                 205
Asp Asn Glu Thr Tyr Val Glu Gln His Glu Val Ala Val Ala Arg Tyr
            210                 215                 220
Cys Asp Leu Pro Ser Lys Leu Gly His Lys Leu Asn Gly Met Asp Glu
225                 230                 235                 240
Ala Asp Thr Arg Ile Gly Val Thr Ile Tyr Lys Tyr Asp Asp Asn Ala
                245                 250                 255
Met Ser Val Val Arg Lys Ala Ile Glu Gln Asp Ala Lys Ala Ala Pro
            260                 265                 270
Asp Val Gln Leu Leu Met Asn Asp Ser Gln Asn Asp Gln Ser Lys Gln
            275                 280                 285
Asn Asp Gln Ile Asp Val Leu Leu Ala Lys Gly Val Lys Ala Leu Ala
        290                 295                 300
Ile Asn Leu Val Asp Pro Ala Ala Gly Thr Val Ile Glu Lys Ala
305                 310                 315                 320
Arg Gly Gln Asn Val Pro Val Phe Phe Asn Lys Glu Pro Ser Arg
                325                 330                 335
Lys Ala Leu Asp Ser Tyr Asp Lys Ala Tyr Tyr Val Gly Thr Asp Ser
            340                 345                 350
Lys Glu Ser Gly Ile Ile Gln Gly Asp Leu Ile Ala Lys His Trp Ala
            355                 360                 365
Ala Asn Gln Gly Trp Asp Leu Asn Lys Asp Gly Gln Ile Gln Phe Val
        370                 375                 380
Leu Leu Lys Gly Glu Pro Gly His Pro Asp Ala Glu Ala Arg Thr Thr
385                 390                 395                 400
Tyr Val Ile Lys Glu Leu Asn Asp Lys Gly Ile Lys Thr Glu Gln Leu
                405                 410                 415
Gln Leu Asp Thr Ala Met Trp Asp Thr Ala Gln Ala Lys Asp Lys Met
            420                 425                 430
Asp Ala Trp Leu Ser Gly Pro Asn Ala Asn Lys Ile Glu Val Val Ile
        435                 440                 445
Ala Asn Asn Asp Ala Met Ala Met Gly Ala Val Glu Ala Leu Lys Ala
    450                 455                 460
His Asn Lys Ser Ser Ile Pro Val Phe Gly Val Asp Ala Leu Pro Glu
465                 470                 475                 480
Ala Leu Ala Leu Val Lys Ser Gly Ala Leu Ala Gly Thr Val Leu Asn
            485                 490                 495
Asp Ala Asn Asn Gln Ala Lys Ala Thr Phe Asp Leu Ala Lys Asn Leu
        500                 505                 510
Ala Asp Met Val Ser Lys Gly Glu Glu Leu Phe Thr Gly Val Val Pro
            515                 520                 525
Ile Leu Val Glu Leu Asp Gly Asp Val Asn Gly His Lys Phe Ser Val
        530                 535                 540
Arg Gly Glu Gly Glu Gly Asp Ala Thr Asn Gly Lys Leu Thr Leu Lys
545                 550                 555                 560
Phe Ile Cys Thr Thr Gly Lys Leu Pro Val Pro Trp Pro Thr Leu Val
                565                 570                 575
Thr Thr Phe Gly Tyr Gly Val Ala Cys Phe Ser Arg Tyr Pro Asp His
            580                 585                 590
```

```
Met Lys Gln His Asp Phe Phe Lys Ser Ala Met Pro Glu Gly Tyr Val
        595                 600                 605

Gln Glu Arg Thr Ile Ser Phe Lys Asp Asp Gly Thr Tyr Lys Thr Arg
        610                 615                 620

Ala Glu Val Lys Phe Glu Gly Asp Thr Leu Val Asn Arg Ile Glu Leu
625                 630                 635                 640

Lys Gly Ile Asp Phe Lys Glu Asp Gly Asn Ile Leu Gly His Lys Leu
                645                 650                 655

Glu Tyr Asn Phe Asn Ser His Asn Val Tyr Ile Thr Ala Asp Lys Gln
                660                 665                 670

Lys Asn Gly Ile Lys Ala Asn Phe Lys Ile Arg His Asn Val Glu Asp
                675                 680                 685

Gly Ser Val Gln Leu Ala Asp His Tyr Gln Gln Asn Thr Pro Ile Gly
                690                 695                 700

Asp Gly Pro Val Leu Leu Pro Asp Asn His Tyr Leu Ser His Gln Ser
705                 710                 715                 720

Ala Leu Ser Lys Asp Pro Asn Glu Lys Arg Asp His Met Val Leu Leu
                725                 730                 735

Glu Phe Val Thr Ala Ala Gly Ile Thr His Gly Met Asp Gly Ala Ala
                740                 745                 750

Asp Gly Thr Asn Trp Lys Ile Asp Asn Lys Val Val Arg Val Pro Tyr
                755                 760                 765

Val Gly Val Asp Lys Asp Asn Leu Ala Glu Phe Ser Lys Lys
                770                 775                 780

<210> SEQ ID NO 7
<211> LENGTH: 231
<212> TYPE: PRT
<213> ORGANISM: Artificial Sequence
<220> FEATURE:
<223> OTHER INFORMATION: Synthetic acceptor-fluorophore amino acid
      sequence 66
<220> FEATURE:
<221> NAME/KEY: MISC_FEATURE
<222> LOCATION: (1)..(1)
<223> OTHER INFORMATION: Xaa can be Gly or Val
<220> FEATURE:
<221> NAME/KEY: MISC_FEATURE
<222> LOCATION: (2)..(2)
<223> OTHER INFORMATION: Xaa can be Glu or Ser
<220> FEATURE:
<221> NAME/KEY: MISC_FEATURE
<222> LOCATION: (11)..(11)
<223> OTHER INFORMATION: Xaa can be Thr or Met
<220> FEATURE:
<221> NAME/KEY: MISC_FEATURE
<222> LOCATION: (28)..(28)
<223> OTHER INFORMATION: Xaa can be His or Ser
<220> FEATURE:
<221> NAME/KEY: MISC_FEATURE
<222> LOCATION: (41)..(41)
<223> OTHER INFORMATION: Xaa can be Asn or Met
<220> FEATURE:
<221> NAME/KEY: MISC_FEATURE
<222> LOCATION: (45)..(45)
<223> OTHER INFORMATION: Xaa can be Val or Ala
<220> FEATURE:
<221> NAME/KEY: MISC_FEATURE
<222> LOCATION: (61)..(61)
<223> OTHER INFORMATION: Xaa can be Cys or Ser
<220> FEATURE:
<221> NAME/KEY: MISC_FEATURE
<222> LOCATION: (104)..(104)
<223> OTHER INFORMATION: Xaa can be Val or Ala
<220> FEATURE:
<221> NAME/KEY: MISC_FEATURE
```

```
<222> LOCATION: (121)..(121)
<223> OTHER INFORMATION: Xaa can be Leu or Ile
<220> FEATURE:
<221> NAME/KEY: MISC_FEATURE
<222> LOCATION: (158)..(158)
<223> OTHER INFORMATION: Xaa can be Cys or Ala
<220> FEATURE:
<221> NAME/KEY: MISC_FEATURE
<222> LOCATION: (171)..(171)
<223> OTHER INFORMATION: Xaa can be His or Ile
<220> FEATURE:
<221> NAME/KEY: MISC_FEATURE
<222> LOCATION: (194)..(194)
<223> OTHER INFORMATION: Xaa can be Phe or Tyr
<220> FEATURE:
<221> NAME/KEY: MISC_FEATURE
<222> LOCATION: (207)..(207)
<223> OTHER INFORMATION: Xaa can be Asn or Lys
<220> FEATURE:
<221> NAME/KEY: MISC_FEATURE
<222> LOCATION: (231)..(231)
<223> OTHER INFORMATION: Xaa can be Lys or Arg

<400> SEQUENCE: 7

Xaa Xaa Glu Leu Ile Lys Glu Asn Met His Xaa Lys Leu Tyr Met Glu
1               5                   10                  15

Gly Thr Val Asn Asn His His Phe Lys Cys Thr Xaa Glu Gly Glu Gly
            20                  25                  30

Lys Pro Tyr Glu Gly Thr Gln Thr Xaa Arg Ile Lys Xaa Val Glu Gly
        35                  40                  45

Gly Pro Leu Pro Phe Ala Phe Asp Ile Leu Ala Thr Xaa Phe Met Tyr
    50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Xaa Thr Gln Asp Thr Ser Leu Gln Asp
            100                 105                 110

Gly Cys Leu Ile Tyr Asn Val Lys Xaa Arg Gly Val Asn Phe Pro Ser
        115                 120                 125

Asn Gly Pro Val Met Gln Lys Lys Thr Leu Gly Trp Glu Ala Ser Thr
    130                 135                 140

Glu Thr Leu Tyr Pro Ala Asp Gly Gly Leu Glu Gly Arg Xaa Asp Met
145                 150                 155                 160

Ala Leu Lys Leu Val Gly Gly His Leu Xaa Cys Asn Leu Lys Thr
                165                 170                 175

Thr Tyr Arg Ser Lys Lys Pro Ala Lys Asn Leu Lys Met Pro Gly Val
                180                 185                 190

Tyr Xaa Val Asp Arg Arg Leu Glu Arg Ile Lys Glu Ala Asp Xaa Glu
        195                 200                 205

Thr Tyr Val Glu Gln His Glu Val Ala Val Ala Arg Tyr Cys Asp Leu
    210                 215                 220

Pro Ser Lys Leu Gly His Xaa
225                 230

<210> SEQ ID NO 8
<211> LENGTH: 6
<212> TYPE: PRT
<213> ORGANISM: Artificial Sequence
<220> FEATURE:
<223> OTHER INFORMATION: Synthetic linker sequence 72

<400> SEQUENCE: 8
```

```
Leu Asn Gly Met Asp Glu
1               5

<210> SEQ ID NO 9
<211> LENGTH: 274
<212> TYPE: PRT
<213> ORGANISM: Artificial Sequence
<220> FEATURE:
<223> OTHER INFORMATION: Synthetic glucose-binding-region sequence 62a
<220> FEATURE:
<221> NAME/KEY: MISC_FEATURE
<222> LOCATION: (16)..(16)
<223> OTHER INFORMATION: Xaa can be a hydrophillic or an amidic amino
      acid (e.g., Gln or Asn), or can be Ala or Val

<400> SEQUENCE: 9

Ala Asp Thr Arg Ile Gly Val Thr Ile Tyr Lys Tyr Asp Asp Asn Xaa
1               5                   10                  15

Met Ser Val Val Arg Lys Ala Ile Glu Gln Asp Ala Lys Ala Ala Pro
            20                  25                  30

Asp Val Gln Leu Leu Met Asn Asp Ser Gln Asn Asp Gln Ser Lys Gln
        35                  40                  45

Asn Asp Gln Ile Asp Val Leu Leu Ala Lys Gly Val Lys Ala Leu Ala
    50                  55                  60

Ile Asn Leu Val Asp Pro Ala Ala Gly Thr Val Ile Glu Lys Ala
65                  70                  75                  80

Arg Gly Gln Asn Val Pro Val Val Phe Phe Asn Lys Glu Pro Ser Arg
                85                  90                  95

Lys Ala Leu Asp Ser Tyr Asp Lys Ala Tyr Tyr Val Gly Thr Asp Ser
            100                 105                 110

Lys Glu Ser Gly Ile Ile Gln Gly Asp Leu Ile Ala Lys His Trp Ala
        115                 120                 125

Ala Asn Gln Gly Trp Asp Leu Asn Lys Asp Gly Gln Ile Gln Phe Val
    130                 135                 140

Leu Leu Lys Gly Glu Pro Gly His Pro Asp Ala Glu Ala Arg Thr Thr
145                 150                 155                 160

Tyr Val Ile Lys Glu Leu Asn Asp Lys Gly Ile Lys Thr Glu Gln Leu
                165                 170                 175

Gln Leu Asp Thr Ala Met Trp Asp Thr Ala Gln Ala Lys Asp Lys Met
            180                 185                 190

Asp Ala Trp Leu Ser Gly Pro Asn Ala Asn Lys Ile Glu Val Val Ile
        195                 200                 205

Ala Asn Asn Asp Ala Met Ala Met Gly Ala Val Glu Ala Leu Lys Ala
    210                 215                 220

His Asn Lys Ser Ser Ile Pro Val Phe Gly Val Asp Ala Leu Pro Glu
225                 230                 235                 240

Ala Leu Ala Leu Val Lys Ser Gly Ala Leu Ala Gly Thr Val Leu Asn
                245                 250                 255

Asp Ala Asn Asn Gln Ala Lys Ala Thr Phe Asp Leu Ala Lys Asn Leu
            260                 265                 270

Ala Asp

<210> SEQ ID NO 10
<211> LENGTH: 231
<212> TYPE: PRT
<213> ORGANISM: Artificial Sequence
<220> FEATURE:
<223> OTHER INFORMATION: Synthetic donor-fluorophore amino acid sequence
```

<400> SEQUENCE: 10

```
Gly Glu Glu Leu Phe Thr Gly Val Val Pro Ile Leu Val Glu Leu Asp
1               5                   10                  15

Gly Asp Val Asn Gly His Lys Phe Ser Val Arg Gly Glu Gly Glu Gly
            20                  25                  30

Asp Ala Thr Asn Gly Lys Leu Thr Leu Lys Phe Ile Cys Thr Thr Gly
        35                  40                  45

Lys Leu Pro Val Pro Trp Pro Thr Leu Val Thr Thr Phe Gly Tyr Gly
    50                  55                  60

Val Ala Cys Phe Ser Arg Tyr Pro Asp His Met Lys Gln His Asp Phe
65                  70                  75                  80

Phe Lys Ser Ala Met Pro Glu Gly Tyr Val Gln Glu Arg Thr Ile Ser
                85                  90                  95

Phe Lys Asp Asp Gly Thr Tyr Lys Thr Arg Ala Glu Val Lys Phe Glu
            100                 105                 110

Gly Asp Thr Leu Val Asn Arg Ile Glu Leu Lys Gly Ile Asp Phe Lys
        115                 120                 125

Glu Asp Gly Asn Ile Leu Gly His Lys Leu Glu Tyr Asn Phe Asn Ser
    130                 135                 140

His Asn Val Tyr Ile Thr Ala Asp Lys Gln Lys Asn Gly Ile Lys Ala
145                 150                 155                 160

Asn Phe Lys Ile Arg His Asn Val Glu Asp Gly Ser Val Gln Leu Ala
                165                 170                 175

Asp His Tyr Gln Gln Asn Thr Pro Ile Gly Asp Gly Pro Val Leu Leu
            180                 185                 190

Pro Asp Asn His Tyr Leu Ser His Gln Ser Ala Leu Ser Lys Asp Pro
        195                 200                 205

Asn Glu Lys Arg Asp His Met Val Leu Leu Glu Phe Val Thr Ala Ala
    210                 215                 220

Gly Ile Thr His Gly Met Asp
225                 230
```

<210> SEQ ID NO 11
<211> LENGTH: 33
<212> TYPE: PRT
<213> ORGANISM: Artificial Sequence
<220> FEATURE:
<223> OTHER INFORMATION: Synthetic glucose-binding-region sequence 62b

<400> SEQUENCE: 11

```
Gly Ala Ala Asp Gly Thr Asn Trp Lys Ile Asp Asn Lys Val Val Arg
1               5                   10                  15

Val Pro Tyr Val Gly Val Asp Lys Asp Asn Leu Ala Glu Phe Ser Lys
            20                  25                  30

Lys
```

<210> SEQ ID NO 12
<211> LENGTH: 21
<212> TYPE: PRT
<213> ORGANISM: Artificial Sequence
<220> FEATURE:
<223> OTHER INFORMATION: Synthetic signal peptide

```
<400> SEQUENCE: 12

Met Trp Trp Arg Leu Trp Trp Leu Leu Leu Leu Leu Leu Leu Leu Trp
1               5                   10                  15

Pro Met Val Trp Ala
            20
```